United States Patent
Chen et al.

(10) Patent No.: US 10,130,687 B2
(45) Date of Patent: Nov. 20, 2018

(54) COMPOSITIONS AND METHODS FOR THE TREATMENT OF ORTHOPEDIC DISEASE OR INJURY

(75) Inventors: Qian Chen, Barrington, RI (US); Chathuraka T. Jayasuriya, North Providence, RI (US)

(73) Assignee: Rhode Island Hospital, Providence, RI (US)

( * ) Notice: Subject to any disclaimer, the term of this patent is extended or adjusted under 35 U.S.C. 154(b) by 0 days.

(21) Appl. No.: 13/976,617

(22) PCT Filed: Jan. 5, 2012

(86) PCT No.: PCT/US2012/020353
§ 371 (c)(1),
(2), (4) Date: Jul. 16, 2013

(87) PCT Pub. No.: WO2012/094511
PCT Pub. Date: Jul. 12, 2012

(65) Prior Publication Data
US 2013/0288972 A1 Oct. 31, 2013

Related U.S. Application Data

(60) Provisional application No. 61/430,134, filed on Jan. 5, 2011.

(51) Int. Cl.
| | | |
|---|---|---|
| *A61K 38/39* | (2006.01) | |
| *A61K 38/17* | (2006.01) | |
| *C07K 14/78* | (2006.01) | |
| *A61P 19/02* | (2006.01) | |
| *A61K 48/00* | (2006.01) | |

(52) U.S. Cl.
CPC .............. *A61K 38/39* (2013.01); *A61K 38/17* (2013.01); *C07K 14/78* (2013.01); *A61K 48/005* (2013.01)

(58) Field of Classification Search
None
See application file for complete search history.

(56) References Cited

U.S. PATENT DOCUMENTS

| | | |
|---|---|---|
| 4,737,323 A | 4/1988 | Martin et al. |
| 4,837,028 A | 6/1989 | Allen |
| 4,868,116 A | 9/1989 | Morgan et al. |
| 4,980,286 A | 12/1990 | Morgan et al. |
| 5,399,346 A | 3/1995 | Anderson et al. |
| 5,460,959 A | 10/1995 | Mulligan et al. |
| 5,677,158 A | 10/1997 | Zhou et al. |
| 5,981,263 A | 11/1999 | Hillman et al. |
| 6,309,634 B1 | 10/2001 | Bankiewicz et al. |
| 6,451,306 B1 | 9/2002 | Tuszynski et al. |
| 6,555,674 B2 | 4/2003 | Tornoe |
| 2003/0203380 A1 | 10/2003 | Stefansson |
| 2007/0099882 A1 | 5/2007 | Gurney et al. |
| 2009/0203590 A1* | 8/2009 | Moses et al. ................... 514/12 |
| 2011/0144752 A1 | 6/2011 | Defelice et al. |
| 2011/0237701 A1 | 9/2011 | Sato et al. |

FOREIGN PATENT DOCUMENTS

| | | |
|---|---|---|
| WO | 9206180 A1 | 4/1992 |
| WO | 9314188 A1 | 7/1993 |
| WO | 9320221 A1 | 10/1993 |
| WO | 9524929 A2 | 9/1995 |
| WO | 9530761 A2 | 11/1995 |

OTHER PUBLICATIONS

Kleemann-Fischer et al., Arch. Biochem. Biophys., 2001, vol. 387(2):209-215.*
Boesen, Jan J.B. et al., "Circumvention of chemotherapy-induced myelosuppression by transfer of the mdr 1 gene," Biotherapy, vol. 6:291-302 (1994).
Fresquet, Maryline et al., "Structural and Functional Characterisation of Recombinant Matrilin-3 A-Domain and Implications for Human Genetic Bone Diseases," J. Biol. Chem., vol. 282(48):34634-34643 (2007).
GeneBank Accession No. NM_002379.3.
GeneBank Accession No. NM_002380.3.
GeneBank Accession No. NM_002381.4.
GeneBank Accession No. NM_003833.4.
GeneBank Accession No. NM_030583.2.
GeneBank Accession No. NM_030590.3.
GeneBank Accession No. NM_030592.3.
GeneBank Accession No. NP_002372.1.
Klatt, Andreas R. et al., "Molecular Structure and Tissue Distribution of Matrilin-3, a Filament-forming Extracellular Matrix Protein Expressed during Skeletal Development," The Journal of Biological Chemistry, vol. 275(6):3999-4006 (2000).
Mrosek, Eike H. et al., "Porous Tantalum and Poly-epsilon-Caprolactone Biocomposites for Osteochondral Defect Repair: Preliminary Studies in Rabbits," Journal of Orthopaedic Research, vol. 28:141-148 (2010).
Wagener, Raimund. et al., "The Matrilins—Adaptor Protein in The Extracellular Matrix." FEBS Letters. vol. 579(15):3323-3329 (2005).
Armelin, H. Pituitary extracts and steroid hormones in the control of 3T3 cell growth. Proc Natl Acad Sci U S A. Sep. 1973;70(9):2702-6.
Banerji et al., Expression of a beta-globin gene is enhanced by remote SV40 DNA sequences. Cell. Dec. 1981;27(2 Pt 1):299-308.
Benoist et al., In vivo sequence requirements of the SV40 early promotor region. Nature. Mar. 26, 1981;290(5804):304-10.

(Continued)

*Primary Examiner* — Xiaozhen Xie
(74) *Attorney, Agent, or Firm* — Mintz, Levin, Cohn, Ferris, Glovsky and Popeo, P.C.; Ingrid A. Beattie

(57) ABSTRACT

Methods for reducing the severity of an arthritic condition or repairing an osteochondral defect are carried out by administering to a subject compositions comprising a member of the matrilin family of proteins, e.g., a matrilin protein, fragment thereof, or nucleic acid encoding the protein or fragment.

6 Claims, 13 Drawing Sheets
Specification includes a Sequence Listing.

(56) References Cited

OTHER PUBLICATIONS

Boesen et al., Circumvention of chemotherapy-induced myelosuppression by transfer of the mdr1 gene. Biotherapy. 1993;6(4):291-302.

Breathnach et al., Organization and expression of eucaryotic split genes coding for proteins. Annu Rev Biochem. 1981;50:349-83.

Capecchi et al., In: Enhancer and Eukaryotic Gene Expression, Gulzman and Shenk, eds., pp. 101-102. (1991).

Chua et al., Tumor necrosis factor-alpha induces mRNA for collagenase and TIMP in human skin fibroblasts. Connect Tissue Res. 1990;25(2):161-70.

Corden et al., Promoter sequences of eukaryotic protein-coding genes. Science. Sep. 19, 1980;209(4463):1406-14.

De Wet et al., The mRNAs for the pro-alpha 1(I) and pro-alpha 2(I) chains of type I procollagen are translated at the same rate in normal human fibroblasts and in fibroblasts from two variants of osteogenesis imperfecta with altered steady state ratios of the two mRNAs. J Biol Chem. Dec. 10, 1983;258(23)14385-9.

Elias et al., Regulation of human lung fibroblast collagen production by recombinant interleukin-1, tumor necrosis factor, and interferon-gamma. Ann N Y Acad Sci. 1990;580:233-44.

Fraley et al., New generation liposomes: the engineering of an efficient vehicle for intracellular delivery of nucleic acids. Trends in Bichemical Sciences. 1981;6:77-80.

Fromm et al., Deletion mapping of DNA regions required for SV40 early region promoter function in vivo. J Mol Appl Genet. 1982;1(5):457-81.

Goldspiel et al., Human gene therapy. Clin Pharm. Jul. 1993;12(7):488-505.

Gruss et al., Simian virus 40 tandem repeated sequences as an element of the early promoter. Proc Natl Acad Sci U S A. Feb. 1981;78(2):943-7.

Howard et al., Intracerebral drug delivery in rats with lesion-induced memory deficits. J Neurosurg. Jul. 1989;71(1):105-12.

Jo et al., Epigenetic regulation of gene structure and function with a cell-permeable Cre recombinase. Nat Biotechnol. Oct. 2001;19(10):929-33.

Joliot et al., Antennapedia homeobox peptide regulates neural morphogenesis. Proc Natl Acad Sci U S A. Mar. 1, 1991;88(5):1864-8.

Jolly et al., Elements in the long terminal repeat of murine retroviruses enhance stable transformation by thymidine kinase gene. Nucleic Acids Res. Mar. 25, 1983;11(6):1855-72.

Kessler et al., Tissue engineering and cartilage. Organogenesis. Jan. 2008;4(1):28-32.

Kiem et al., Retrovirus-mediated gene transduction into canine peripheral blood repopulating cells. Blood. Mar. 15, 1994;83(6):1467-73.

Kligman et al., Intra-synovial, compared to intra-articular morphine provides better pain relief following knee arthroscopy menisectomy. Can J Anaesth. Apr. 2002;49(4):380-3.

Koch, A. The role of angiogenesis in rheumatoid arthritis: recent developments. Ann Rheum Dis. Nov. 2000;59 Suppl 1:i65-71.

Koller et al., Inactivating the beta 2-microglobulin locus in mouse embryonic stem cells by homologous recombination. Proc Natl Acad Sci U S A. Nov. 1989;86(22):8932-5.

Kozarsky et al., Gene therapy: adenovirus vectors. Curr Opin Genet Dev. Jun. 1993;3(3):499-503.

Lee et al., Regeneration of the articular surface of the rabbit synovial joint by cell homing: a proof of concept study. Lancet. Aug. 7, 2010;376(9739):440-8.

Loeffler et al., Gene transfer into primary and established mammalian cell lines with lipopolyamine-coated DNA. Methods Enzymol. 1993;217:599-618.

Maniatis et al., Molecular Cloning, A Laboratory Manual. 1982;133-134.

Mannino et al., Liposome mediated gene transfer. Biotechniques. Jul.-Aug. 1988;6(7):682-90.

Maxam et al., Sequencing end-labeled DNA with base-specific chemical cleavages. Methods Enzymol. 1980;65(1):499-560.

Messing et al., A system for shotgun DNA sequencing. Nucleic Acids Res. Jan. 24, 1981;9(2):309-21.

Miller et al., Use of retroviral vectors for gene transfer and expression. Methods Enzymol. 1993;217:581-99.

Moreau et al., The SV40 72 base repair repeat has a striking effect on gene expression both in SV40 and other chimeric recombinants. Nucleic Acids Res. Nov. 25, 1981;9(22):6047-68.

Pluck, A. Conditional mutagenesis in mice: the Cre/loxP recombination system. Int J Exp Pathol. Dec. 1996;77(6):269-78.

Prockop et al., Heritable diseases of collagen. N Engl J Med. Aug. 6, 1984;311(6):376-86.

Rossi et al., Identification of a cell-specific transcriptional enhancer in the first intron of the mouse alpha 2 (type I) collagen gene. Proc Natl Acad Sci U S A. Aug. 1987;84(16):5590-4.

Saudek et al., A preliminary trial of the programmable implantable medication system for insulin delivery. N Engl J Med. Aug. 31, 1989;321(9):574-9.

Schmidt et al., Regulation of a collagen gene promoter by the product of viral mos oncogene. Nature. Mar. 21-27, 1985;314(6008):286-9.

Seliger et al., Gamma interferon regulates long terminal repeat-controlled oncogene expression in transformed mouse fibroblasts at the level of mRNA transcription. J Virol. Feb. 1988;62(2):619-21.

Seliger et al., Tumor necrosis factor-alpha affects LTR-controlled oncogene expression in transformed mouse fibroblasts at the post-transcriptional level. J Immunol. Sep. 15, 1988;141(6):2138-44.

Smith et al., Characterization of collagen synthesized by normal and chemically transformed rat liver epithelial cell lines. Biochemistry. Apr. 29, 1980;19(9)1820-5.

Van de Breevaart Bravenboer J, In der Maur et al., Improved cartilage integration and interfacial strength after enzymatic treatment in a cartilage transplantation model. Arthritis Res Ther. 2004;6(5):R469-76.

Walsh et al., Gene therapy for human hemoglobinopathies. Proc Soc Exp Biol Med. Dec. 1993;204(3):289-300.

Wu et al., Receptor-mediated in vitro gene transformation by a soluble DNA carrier system. J Biol Chem. Apr. 5, 1987;262(10):4429-32.

Yang et al., Matrilin-3 inhibits chondrocyte hypertrophy as a bone morphogenetic protein-2 antagonist. J Biol Chem. Dec. 12, 2014;289(50):34768-79.

Zijlstra et al., Germ-line transmission of a disrupted beta 2-microglobulin gene produced by homologous recombination in embryonic stem cells. Nature. Nov. 23, 1989;342(6248):435-8.

\* cited by examiner

SEQUENCE LISTING

<160> NUMBER OF SEQ ID NOS: 11

<210> SEQ ID NO 1
<211> LENGTH: 486
<212> TYPE: PRT
<213> ORGANISM: Homo sapiens

<400> SEQUENCE: 1

```
Met Pro Arg Pro Ala Pro Ala Arg Arg Leu Pro Gly Leu Leu Leu Leu
1               5                   10                  15

Leu Trp Pro Leu Leu Leu Pro Ser Ala Ala Pro Asp Pro Val Ala
            20                  25                  30

Arg Pro Gly Phe Arg Arg Leu Glu Thr Arg Gly Pro Gly Gly Ser Pro
            35                  40                  45

Gly Arg Arg Pro Ser Pro Ala Ala Pro Asp Gly Ala Pro Ala Ser Gly
        50                  55                  60

Thr Ser Glu Pro Gly Arg Ala Arg Gly Ala Gly Val Cys Lys Ser Arg
65                  70                  75                  80

Pro Leu Asp Leu Val Phe Ile Ile Asp Ser Ser Arg Ser Val Arg Pro
                85                  90                  95

Leu Glu Phe Thr Lys Val Lys Thr Phe Val Ser Arg Ile Ile Asp Thr
            100                 105                 110

Leu Asp Ile Gly Pro Ala Asp Thr Arg Val Ala Val Val Asn Tyr Ala
            115                 120                 125

Ser Thr Val Lys Ile Glu Phe Gln Leu Gln Ala Tyr Thr Asp Lys Gln
        130                 135                 140

Ser Leu Lys Gln Ala Val Gly Arg Ile Thr Pro Leu Ser Thr Gly Thr
145                 150                 155                 160

Met Ser Gly Leu Ala Ile Gln Thr Ala Met Asp Glu Ala Phe Thr Val
                165                 170                 175

Glu Ala Gly Ala Arg Gly Pro Ser Ser Asn Ile Pro Lys Val Ala Ile
            180                 185                 190

Ile Val Thr Asp Gly Arg Pro Gln Asp Gln Val Asn Glu Val Ala Ala
            195                 200                 205

Arg Ala Gln Ala Ser Gly Ile Glu Leu Tyr Ala Val Gly Val Asp Arg
        210                 215                 220

Ala Asp Met Ala Ser Leu Lys Met Met Ala Ser Glu Pro Leu Glu Glu
225                 230                 235                 240

His Val Phe Tyr Val Glu Thr Tyr Gly Val Ile Glu Lys Leu Ser Ser
                245                 250                 255

Arg Phe Gln Glu Thr Phe Cys Ala Leu Asp Pro Cys Val Leu Gly Thr
            260                 265                 270

His Gln Cys Gln His Val Cys Ile Ser Asp Gly Glu Gly Lys His His
            275                 280                 285

Cys Glu Cys Ser Gln Gly Tyr Thr Leu Asn Ala Asp Lys Lys Thr Cys
        290                 295                 300

Ser Ala Leu Asp Arg Cys Ala Leu Asn Thr His Gly Cys Glu His Ile
305                 310                 315                 320

Cys Val Asn Asp Arg Ser Gly Ser Tyr His Cys Glu Cys Tyr Glu Gly
                325                 330                 335

Tyr Thr Leu Asn Glu Asp Arg Lys Thr Cys Ser Ala Gln Asp Lys Cys
            340                 345                 350

Ala Leu Gly Thr His Gly Cys Gln His Ile Cys Val Asn Asp Arg Thr
            355                 360                 365
```

```
Gly Ser His His Cys Glu Cys Tyr Glu Gly Tyr Thr Leu Asn Ala Asp
    370                 375                 380

Lys Lys Thr Cys Ser Val Arg Asp Lys Cys Ala Leu Gly Ser His Gly
385                 390                 395                 400

Cys Gln His Ile Cys Val Ser Asp Gly Ala Ala Ser Tyr His Cys Asp
                405                 410                 415

Cys Tyr Pro Gly Tyr Thr Leu Asn Glu Asp Lys Lys Thr Cys Ser Ala
            420                 425                 430

Thr Glu Glu Ala Arg Arg Leu Val Ser Thr Glu Asp Ala Cys Gly Cys
        435                 440                 445

Glu Ala Thr Leu Ala Phe Gln Asp Lys Val Ser Ser Tyr Leu Gln Arg
    450                 455                 460

Leu Asn Thr Lys Leu Asp Asp Ile Leu Glu Lys Leu Lys Ile Asn Glu
465                 470                 475                 480

Tyr Gly Gln Ile His Arg
                485
```

<210> SEQ ID NO 2
<211> LENGTH: 2600
<212> TYPE: DNA
<213> ORGANISM: Homo sapiens

<400> SEQUENCE: 2

```
aaatccgagc ctcgcgtggg ctcctggccc ccgacggaca ccaccaggcc cacggagccc      60
accatgccgc gcccggcccc cgcgcgccgc ctcccgggac tcctcctgct gctctggccg     120
ctgctgctgc tgcccccgc cgcccccgac ccgtggccc gccgggcctt ccggaggctg      180
gagacccgag gtcccggggg cagccctgga cgccgcccct ctcctgcggc tcccgacggc     240
gcgcccgctt ccgggaccag cgagcctggc cgcgcccgcg gtgcaggtgt ttgcaagagc     300
agacccttgg acctggtgtt tatcattgat agttctcgta gcgtacggcc cctggaattc     360
accaaagtga aaacttttgt ctcccggata atcgacactc tggacattgg gccagccgac     420
acgcgggtgg cagtggtgaa ctatgctagc actgtgaaga tcgagttcca actccaggcc     480
tacacagata agcagtccct gaagcaggcc gtgggtcgaa tcacacccct tgtcaacagg     540
accatgtcag gcctagccat ccagacagca atggacgaag ccttcacagt ggaggcaggg     600
gctcgagagc cctcttctaa catccctaag gtggccatca ttgttacaga tgggaggccc     660
caggaccagg tgaatgaggt ggcggctcgg gcccaagcat ctggtattga gctctatgct     720
gtgggcgtgg accgggcaga catggcgtcc ctcaagatga tggccagtga gccccctagag     780
gagcatgttt tctacgtgga gacctatggg gtcattgaga aactttcctc tagattccag     840
gaaaccttct gtgcgctgga ccctgtgtg cttggaacac accagtgcca gcacgtctgc     900
atcagtgatg gggaaggcaa gcaccactgt gagtgtagcc aaggatacac cttgaatgcc     960
gacaagaaaa cgtgttcagc tcttgatagg tgtgctctta cacccacgg atgtgagcac    1020
atctgtgtga atgacagaag tggctcttat cattgtgagt gctatgaagg ttataccttg    1080
aatgaagaca ggaaaacttg ttcagctcaa gataaatgtg ctttgggtac ccatgggtgt    1140
cagcacattt gtgtgaatga cagaacaggg tccatcatt gtgaatgcta tgagggctac    1200
actctgaatg cagataaaaa aacatgttca gtccgtgaca agtgtgccct aggctctcat    1260
ggttgccagc acatttgtgt gagtgatggg gccgcatcct accactgtga ttgctatcct    1320
ggctacacct taaatgagga caagaaaaca tgttcagcca ctgaggaagc acgaagactt    1380
gtttccactg aagatgcttg tggatgtgaa gctacactgg cattccagga caaggtcagc    1440
```

```
tcgtatcttc aaagactgaa cactaaactt gatgacattt tggagaagtt gaaaataaat    1500
gaatatggac aaatacatcg ttaaattgct ccaatttctc acctgaaaat gtggacagct    1560
tggtgtactt aatactcatg cattcttttg cacacctgtt attgccaatg ttcctgctaa    1620
taatttgcca ttatctgtat taatgcttga atattactgg ataaattgta tgaagatctt    1680
ctgcagaatc agcatgattc ttccaaggaa atacatatgc agatacttat taagagcaaa    1740
ctttagtgtc tctaagttat gactgtgaaa tgattggtag gaaatagaat gaaaagttta    1800
gtgtttcttt atctactaat tgagccattt aattttttaaa tgtttatatt agataaccat    1860
attcacaatg gaaactttag gtctagtttc ttttgatagt atttataata taaatcaatc    1920
ttattactga gagtgcaaat tgtacaaggt atttacacat acaacttcat ataactgaga    1980
tgaatgtaat tttgaactgt ttaacacttt ttgttttttg cttatttgt tggagtatta     2040 ttgaagatgt gatcaataga ttgtaataca catatctaaa aatagttaac acagatcaag    2100
tgaacattac attgccattt ttaattcatt ctggtctttg aaagaaatgt actactaaag    2160
agcactagtt gtgaatttag ggtgttaaac ttttaccaa gtacaaaaat cccaaattca     2220
ctttattatt ttgcttcagg atccaagtga caaagttata tatttataaa attgctataa    2280
atcgacaaaa tctaatgttg tctttttaat gttagtgatc cacctgcctc agcctcccaa    2340
agtgctggga ttacaggctt gaaagtctaa cttttttta cttatatatt tgatacatat      2400
aattcttttg gctttgaaac ttgcaacttt gagaacaaaa cagtccttta aattttgcac    2460
tgctcaattc tgttttttcgt ttgcattgtc tttaatataa taaagttat tacctttaca    2520 tattatcatg tctattttg atgactcatc aattttgtct attaaagata tttctttaaa    2580
ttaaaaaaaa aaaaaaaaa                                                 2600
```

<210> SEQ ID NO 3
<211> LENGTH: 480
<212> TYPE: PRT
<213> ORGANISM: Homo sapiens

<400> SEQUENCE: 3

Trp Asp Glu Gly Ala Gly Gln Gly Trp Ala Gly Pro Leu Asp Ser Gly
1               5                   10                  15

His Leu Cys Arg Thr Arg Pro Thr Asp Leu Val Phe Val Val Asp Ser
            20                  25                  30

Ser Arg Ser Val Arg Pro Val Glu Phe Glu Lys Val Lys Val Phe Leu
        35                  40                  45

Ser Gln Val Ile Glu Ser Leu Asp Val Gly Pro Asn Ala Thr Arg Val
    50                  55                  60

Gly Met Val Asn Tyr Ala Ser Thr Val Lys Gln Glu Phe Ser Leu Arg
65                  70                  75                  80

Ala His Val Ser Lys Ala Ala Leu Leu Gln Ala Val Arg Arg Ile Gln
                85                  90                  95

Pro Leu Ser Thr Gly Thr Met Thr Gly Leu Ala Ile Gln Phe Ala Ile
            100                 105                 110

Thr Lys Ala Phe Gly Asp Ala Glu Gly Gly Arg Ser Arg Ser Pro Asp
        115                 120                 125

Ile Ser Lys Val Val Ile Val Thr Asp Gly Arg Pro Gln Asp Ser
    130                 135                 140

Val Gln Asp Val Ser Ala Arg Ala Arg Ala Ser Gly Val Glu Leu Phe
145                 150                 155                 160

Ala Ile Gly Val Gly Ser Val Asp Lys Ala Thr Leu Arg Gln Ile Ala
            165                 170                 175

Ser Glu Pro Gln Asp Glu His Val Asp Tyr Val Glu Ser Tyr Ser Val
        180                 185                 190

Ile Glu Lys Leu Ser Arg Lys Phe Gln Glu Ala Phe Cys Val Val Ser
        195                 200                 205

Asp Leu Cys Ala Thr Gly Asp His Asp Cys Glu Gln Val Cys Ile Ser
    210                 215                 220

Ser Pro Gly Ser Tyr Thr Cys Ala Cys His Glu Gly Phe Thr Leu Asn
225                 230                 235                 240

Ser Asp Gly Lys Thr Cys Asn Val Cys Ser Gly Gly Gly Ser Ser
                245                 250                 255

Ala Thr Asp Leu Val Phe Leu Ile Asp Gly Ser Lys Ser Val Arg Pro
            260                 265                 270

Glu Asn Phe Glu Leu Val Lys Lys Phe Ile Ser Gln Ile Val Asp Thr
        275                 280                 285

Leu Asp Val Ser Asp Lys Leu Ala Gln Val Gly Leu Val Gln Tyr Ser
        290                 295                 300

Ser Ser Val Arg Gln Glu Phe Pro Leu Gly Arg Phe His Thr Lys Lys
305                 310                 315                 320

Asp Ile Lys Ala Ala Val Arg Asn Met Ser Tyr Met Glu Lys Gly Thr
                325                 330                 335

Met Thr Gly Ala Ala Leu Lys Tyr Leu Ile Asp Asn Ser Phe Thr Val
            340                 345                 350

Ser Ser Gly Ala Arg Pro Gly Ala Gln Lys Val Gly Ile Val Phe Thr
        355                 360                 365

Asp Gly Arg Ser Gln Asp Tyr Ile Asn Asp Ala Ala Lys Lys Ala Lys
    370                 375                 380

Asp Leu Gly Phe Lys Met Phe Ala Val Gly Val Gly Asn Ala Val Glu
385                 390                 395                 400

Asp Glu Leu Arg Glu Ile Ala Ser Glu Pro Val Ala Glu His Tyr Phe
                405                 410                 415

Tyr Thr Ala Asp Phe Lys Thr Ile Asn Gln Ile Gly Lys Lys Leu Gln
            420                 425                 430

Lys Lys Ile Cys Val Glu Glu Asp Pro Cys Ala Cys Glu Ser Leu Val
        435                 440                 445

Lys Phe Gln Ala Lys Val Glu Gly Leu Leu Gln Ala Leu Thr Arg Lys
    450                 455                 460

Leu Glu Ala Val Ser Lys Arg Leu Ala Ile Leu Glu Asn Thr Val Val
465                 470                 475                 480

<210> SEQ ID NO 4
<211> LENGTH: 414
<212> TYPE: PRT
<213> ORGANISM: Homo sapiens

<400> SEQUENCE: 4

Asp Pro Val Ala Arg Pro Gly Phe Arg Arg Leu Glu Thr Arg Gly Pro
1               5                   10                  15

Gly Gly Ser Pro Gly Arg Arg Pro Ser Pro Ala Ala Pro Asp Gly Ala
            20                  25                  30

Pro Ala Ser Gly Thr Ser Glu Pro Gly Arg Ala Arg Gly Ala Gly Val
        35                  40                  45

Cys Lys Ser Arg Pro Leu Asp Leu Val Phe Ile Ile Asp Ser Ser Arg
    50                  55                  60

```
Ser Val Arg Pro Leu Glu Phe Thr Lys Val Lys Thr Phe Val Ser Arg
 65                  70                  75                  80

Ile Ile Asp Thr Leu Asp Ile Gly Pro Ala Asp Thr Arg Val Ala Val
                 85                  90                  95

Val Asn Tyr Ala Ser Thr Val Lys Ile Glu Phe Gln Leu Gln Ala Tyr
            100                 105                 110

Thr Asp Lys Gln Ser Leu Lys Gln Ala Val Gly Arg Ile Thr Pro Leu
        115                 120                 125

Ser Thr Gly Thr Met Ser Gly Leu Ala Ile Gln Thr Ala Met Asp Glu
    130                 135                 140

Ala Phe Thr Val Glu Ala Gly Ala Arg Glu Pro Ser Ser Asn Ile Pro
145                 150                 155                 160

Lys Val Ala Ile Ile Val Thr Asp Gly Arg Pro Gln Asp Gln Val Asn
                165                 170                 175

Glu Val Ala Ala Arg Ala Gln Ala Ser Gly Ile Glu Leu Tyr Ala Val
            180                 185                 190

Gly Val Asp Arg Ala Asp Met Ala Ser Leu Lys Met Met Ala Ser Glu
        195                 200                 205

Pro Leu Glu Glu His Val Phe Tyr Val Glu Thr Tyr Gly Val Ile Glu
    210                 215                 220

Lys Leu Ser Ser Arg Phe Gln Glu Thr Phe Cys Ala Leu Asp Pro Cys
225                 230                 235                 240

Val Leu Gly Thr His Gln Cys Gln His Val Cys Ile Ser Asp Gly Glu
                245                 250                 255

Gly Lys His His Cys Glu Cys Ser Gln Gly Tyr Thr Leu Asn Ala Asp
            260                 265                 270

Lys Lys Thr Cys Ser Ala Leu Asp Arg Cys Ala Leu Asn Thr His Gly
        275                 280                 285

Cys Glu His Ile Cys Val Asn Asp Arg Ser Gly Ser Tyr His Cys Glu
    290                 295                 300

Cys Tyr Glu Gly Tyr Thr Leu Asn Glu Asp Arg Lys Thr Cys Ser Ala
305                 310                 315                 320

Gln Asp Lys Cys Ala Leu Gly Thr His Gly Cys Gln His Ile Cys Val
                325                 330                 335

Asn Asp Arg Thr Gly Ser His His Cys Glu Cys Tyr Glu Gly Tyr Thr
            340                 345                 350

Leu Asn Ala Asp Lys Lys Thr Cys Ser Val Arg Asp Lys Cys Ala Leu
        355                 360                 365

Gly Ser His Gly Cys Gln His Ile Cys Val Ser Asp Gly Ala Ala Ser
    370                 375                 380

Tyr His Cys Asp Cys Tyr Pro Gly Tyr Thr Leu Asn Glu Asp Lys Lys
385                 390                 395                 400

Thr Cys Ser Ala Thr Glu Glu Ala Arg Arg Leu Val His Arg
                405                 410

<210> SEQ ID NO 5
<211> LENGTH: 3830
<212> TYPE: DNA
<213> ORGANISM: Homo sapiens

<400> SEQUENCE: 5
aaccgtgccg gctgctgccc gtgctgccag aactatgagg gtcctctctg gcactagcct      60
catgctctgc agcctgctgc tgctgctcca ggccctgtgc agccctggcc tcgcccccca     120
```

```
gtccagaggc catctctgcc ggacgcggcc cacagacctg gtgtttgttg tcgacagctc    180
tcgcagcgtt cggcctgttg aatttgagaa agtgaaggta ttcctgtccc aggtcatcga    240
gtcgctggac gtggggccca atgccacccg ggtgggcatg gtcaactatg ccagcaccgt    300
gaagcaggag ttctcgctgc gggctcatgt ctccaaggcc gcactgctgc aggctgtgcg    360
ccgtatccag ccgctgtcca caggcaccat gaccggcctg gccatccagt tcgctatcac    420
caaagccttc ggcgatgcag agggtggtcg ttccaggtcc cctgacatca gcaaggtggt    480
catcgtggtg acagacggga ggccccagga cagcgtgcag gacgtgtctg cgcgggcccg    540
ggccagcggc gtcgagctgt tcgccatcgg agtgggcagc gtggacaagg ccacgctgcg    600
gcagatcgcc agcgagccgc aggacgaaca cgtcgattac gtggagagct acagcgtcat    660
cgagaagctg tccaggaagt tccaggaggc cttctgcgtg gtgtcagacc tgtgcgccac    720
aggggaccat gactgtgagc aggtgtgcat cagctccccc ggttcctaca cctgcgcctg    780
ccacgagggc ttcactctga acagcgacgg caagacctgc aatgtctgca gtggtggtgg    840
tggcagctcg gccactgacc tggtcttcct cattgacgga tccaagagtg tgaggccaga    900
gaactttgag ctggtgaaga agttcatcag tcagatcgtg gatacgctgg acgtgtcaga    960
caagctggcc caggtggggc tggtgcagta ctcaagctct gtgcgccagg agttcccccct   1020 gggtcgcttc cacaccaaga aggacatcaa ggcggctgtg cggaatatgt cctacatgga   1080
gaagggcaca atgactgggg ctgctctcaa gtacctcatt gacaattcct tcactgtgtc   1140
cagtggggct aggcccgggg cccagaaggt gggcattgtc ttcactgatg gccggagcca   1200
ggactacatt aatgatgctg ccaagaaggc caaagacctc ggctttaaga tgtttgctgt   1260
gggtgtgggc aatgccgtgg aggatgagct gagggaaata gcctcagagc tgtggcagaa   1320
gcactacttc tacacggctg acttcaagac catcaaccag ataggcaaga agttgcagaa   1380
gaagatctgt gtggaggaag acccgtgtgc ctgcgagtcc ctggtgaaat tccaagccaa   1440
agtggagggg ctgctgcagg ccctgaccag gaaactggaa gctgtgagta gcggctggc   1500 catcctggag aacacagttg tctaaggctg cctgtcacca ctgtggcctc tccaagcgtc   1560
ctgcacgtgt ccgccgtagc tttaccattt tagtgaggga agccagcccg ggggtgggag   1620
ggggtgtgtc tgggtgtgcc tattgagagc gtgtaatggc gtttgggagc tcgtgtgtgt   1680
atgtgtgcgt gtgtgtatgt gtgcatgtgt gtgtgtgtgt gtgtgtgtgc acgtgcgcct   1740
gagggtgggc atgagtcttg ccagaatgtg agtgtgagag tgataatgca ggggtgagtg   1800
tgagagggac tgcgtttgca tttttataat caaaagctta atatattccc atcttttta   1860 gttaacccctt tcttgactct gagtgctgtg aatttcttta ctgatttctc tattctccgg   1920
tgagaaacaa ttaaatgtga tttaacgtaa gcagtgaatg gggctagagg cagtgtggtt   1980
atttggggac cagggaaaag gatggatgaa gatgtggtgg gaggggatgg ttggaaggat   2040
ggtaacagtg gtggtgacag tgatgacagt gaccacacca aaaccagctg gtgtttgtcc   2100
tgccttttca gttacatatt catttagttg acctcatttc acttccagta accttaccca   2160
gaaaagactc aaattatccc cattacaaat gggaaagctg agagtctaaa tgatgaaatg   2220
acttgctcag cagtgggtcg ctgagagaca ggacttgaat ctaggactga agaacatcaa   2280
aagaaaaagg cttcagagaa aaagggcaat gacaccagat aggactcatt tgttcattca   2340
ttcattcgtt cactcattcg ttcaggtatc atgtacttac agggcaatgg cggtgggggg   2400
ggatggtgct gtatgagaca gacgtagttc ctgccctaag agacatacag ttgagcaggg   2460
tgctcatgtc accccccacca gccagaggga ccagccagag gaaaagagag tgggtttagg   2520
```

```
tcgtaccagg ggtttgtgcc tcctcttgat acctgggagc ccacggggtg agtgtgtgtg    2580
tgagatgatg ggaagggctc cagcctgggc ctgggctgcc ctaggtgcct ctcccctccc    2640
gcccccaaca tgccctgttg gagttctgtt tgtttcctgt gcacaggcgg catcacccc     2700 aacccaaagt ccccaacgca gatggcagca gccccacctc agagactgca caagagaaag    2760
actcctggcc ccatgttccc ttcctccagc cctatgtggg gtctgcaggt cacaccctga    2820
gatctcggcc acctcccca  ggcccctgtt ggaccagtgc tgctccggaa tctccatctc    2880
tgtcctctca gagggggagc tttggtgatt ttctgaacct attcttgttt aatggagcat    2940
ttttagtgtt actactagat tcacacttga gagcatgtct aaaaggcttt tacaagaagc    3000
tcagaccaca ccgaaagatc ttcctcggag gcagttcaaa gaggcagaat aacaacacga    3060
acggtaccca agagctacat cagtacaaca gcacaaatac acaagcgcga cttaactggg    3120
gcacagccac cctcgcccc  atgacctgac tccacctcct acacagttca ccaaacccttt    3180 tctctctgtc cgtccctggg gcaggagttt ttctgctgtc caaggaggct ccttgacaca    3240
gccacctgag aagttatgac tctgctcatt cttcctttct tctgagatta ccactcccc    3300 tctcctcccc acacaggtgg ggaggggggag aggcagccat gttgatatgg actgagaagg    3360
ctcagcagtg tgtccccaag gaggaggaga gggtcattag cggacgccat ggcctgggag    3420
ctggcgggca gaagcaacag atgtccctga tgagtggagt cagagatggg gtggaagccc    3480
tgcctgggaa taggacctcg ttcttccctg cccggtgggt ggagtagtgg caggaccttg    3540
tcaccaggct ctgatgaagg cagggaccag cttcttggga tctttcaatc ccaaactctt    3600
gcccttcact catcgcagtt ctccccacgg ctactccagg tcctcttgaa atccgtcctc    3660
tccatggact tcccacatcc ctctctgctc taggtttgat taacagaagg ttgtaaatga    3720
aaaccagcat ctcccgaggg cagccatggt ctactgacag atggcaagtt actttgtaac    3780
ctgtaatttt gttttttga  attttgtata aataaacagg actaaactaa                3830

<210> SEQ ID NO 6
<211> LENGTH: 4122
<212> TYPE: DNA
<213> ORGANISM: Homo sapiens

<400> SEQUENCE: 6
gcgagcgaag ggagcgctct gggatgggac ttggagcaag cggcggcggc ggagacagag      60
gcagaggcag aagctggggc tccgtcctcg cctcccacga gcgatccccg aggagagccg     120
cggccctcgg cgaggcgaag aggccgacga ggaagacccg ggtggctgcg cccctgcctc     180
gcttcccagg cgccggcggc tgcagccttg cccctcttgc tcgccttgaa aatggaaaag     240
atgctcgcag gctgctttct gctgatcctc ggacagatcg tcctcctccc tgccgaggcc     300
agggagcggt cacgtgggag gtccatctct aggggcagac acgctcggac ccacccgcag     360
acggcccttc tggagagttc ctgtgagaac aagcgggcag acctggtttt catcattgac     420
agctctcgca gtgtcaacac ccatgactat gcaaaggtca aggagttcat cgtggacatc     480
ttgcaattct tggacattgg tcctgatgtc acccgagtgg gcctgctcca atatggcagc     540
actgtcaaga atgagttctc cctcaagacc ttcaaggaga agtccgaggt ggagcgtgct     600
gtcaagagga tgcggcatct gtccacgggc accatgactg gctggccat  ccagtatgcc     660 ctgaacatcg cattctcaga agcagagggg gcccggcccc tgagggagaa tgtgccacgg     720
gtcataatga tcgtgacaga tgggagacct caggactccg tggccgaggt ggctgctaag     780
```

```
gcacgggaca cgggcatcct aatctttgcc attggtgtgg gccaggtaga cttcaacacc    840
ttgaagtcca ttgggagtga gccccatgag gaccatgtct tccttgtggc caatttcagc    900
cagattgaga cgctgacctc cgtgttccag aagaagttgt gcacggccca catgtgcagc    960
accctggagc ataactgtgc ccacttctgc atcaacatcc ctggctcata cgtctgcagg   1020
tgcaaacaag gctacattct caactcggat cagacgactt gcagaatcca ggatctgtgt   1080
gccatggagg accacaactg tgagcagctc tgtgtgaatg tgccgggctc cttcgtctgc   1140
cagtgctaca gtggctacgc cctggctgag gatgggaaga ggtgtgtggc tgtggactac   1200
tgtgcctcag aaaaccacgg atgtgaacat gagtgtgtaa atgctgatgg ctcctacctt   1260
tgccagtgcc atgaaggatt tgctcttaac ccagataaaa aaacgtgcac aaagatagac   1320
tactgtgcct catctaatca cggatgtcag cacgagtgtg ttaacacaga tgattcctat   1380
tcctgccact gcctgaaagg ctttaccctg aatccagata agaaaacctg cagaaggatc   1440
aactactgtg cactgaacaa accgggctgt gagcatgagt gcgtcaacat ggaggagagc   1500
tactactgcc gctgccaccg tggctacact ctggacccca tggcaaaaac ctgcagccga   1560
gtggaccact gtgcacagca ggaccatggc tgtgagcagc tgtgtctgaa cacggaggat   1620
tccttcgtct gccagtgctc agaaggcttc ctcatcaacg aggacctcaa gacctgctcc   1680
cgggtggatt actgcctgct gagtgaccat ggttgtgaat actcctgtgt caacatggac   1740
agatcctttg cctgtcagtg tcctgaggga cacgtgctcc gcagcgatgg gaagacgtgt   1800
gcaaaattgg actcttgtgc tctggggac cacggttgtg aacattcgtg tgtaagcagt   1860
gaagattcgt ttgtgtgcca gtgctttgaa ggttatatac tccgtgaaga tggaaaaacc   1920
tgcagaagga aagatgtctg ccaagctata gaccatggct gtgaacacat ttgtgtgaac   1980
agtgatgact catacacgtg cgagtgcttg gagggattcc ggctcgctga ggatgggaaa   2040
cgctgccgaa ggaaggatgt ctgcaaatca acccaccatg gctgcgaaca catttgtgtt   2100
aataatggga attcctacat ctgcaaatgc tcagagggat ttgttctagc tgaggacgga   2160
agacggtgca gaaatgcac tgaaggccca attgacctgg tctttgtgat cgatggatcc   2220
aagagtcttg gagaagagaa ttttgaggtc gtgaagcagt ttgtcactgg aattatagat   2280
tccttgacaa tttcccccaa agccgctcga gtggggctgc tccagtattc cacacaggtc   2340
cacacagagt tcactctgag aaacttcaac tcagccaaag acatgaaaaa agccgtggcc   2400
cacatgaaat acatgggaaa gggctctatg actgggctgg ccctgaaaca catgtttgag   2460
agaagtttta cccaaggaga aggggccagg ccccttttcca aagggtgcc cagagcagcc   2520
attgtgttca ccgacggacg ggctcaggat gacgtctccg agtgggccag taaagccaag   2580
gccaatggta tcactatgta tgctgttggg gtaggaaaag ccattgagga ggaactacaa   2640
gagattgcct ctgagcccac aaacaagcat ctcttctatg ccgaagactt cagcacaatg   2700
gatgagataa gtgaaaaact caagaaaggc atctgtgaag ctctagaaga ctccgatgga   2760
agacaggact ctccagcagg ggaactgcca aaaacggtcc aacagccaac agaatctgag   2820
ccagtcacca taaatatcca agacctactt tcctgttcta attttgcagt gcaacacaga   2880
tatctgtttg aagaagacaa tctttttacgg tctacacaaa agcttcccca ttcaacaaaa   2940
ccttcaggaa gcccttttgga agaaaaacac gatcaatgca aatgtgaaaa ccttataatg   3000
ttccagaacc ttgcaaacga agaagtaaga aaattaacac agcgcttaga agaaatgaca   3060
cagagaatgg aagccctgga aaatcgcctg agatacagat gaagattaga aatcgcgaca   3120
catttgtagt cattgtatca cggattacaa tgaacgcagt gcagagcccc aaagctcagg   3180
```

| | | | | |
|---|---|---|---|---|
| ctattgttaa | atcaataatg | ttgtgaagta | aaacaatcag | tactgagaaa cctggtttgc | 3240 |
| cacagaacaa | agacaagaag | tatacactaa | cttgtataaa | tttatctagg aaaaaaatcc | 3300 |
| ttcagaattc | taagatgaat | ttaccaggtg | agaatgaata | agctatgcaa ggtattttgt | 3360 |
| aatatactgt | ggacacaact | tgcttctgcc | tcatcctgcc | ttagtgtgca atctcatttg | 3420 |
| actatacgat | aaagtttgca | cagtcttact | tctgtagaac | actggccata ggaaatgctg | 3480 |
| tttttttgta | ctggacttta | ccttgatata | tgtatatgga | tgtatgcata aaatcatagg | 3540 |
| acatatgtac | ttgtggaaca | agttggattt | tttatacaat | attaaaattc accacttcag | 3600 |
| agaatggtat | tcagtgcaaa | aattcttagt | ttaactttaa | atggaagata tgtatgtatg | 3660 |
| agaaatggcc | aacatgccta | tgaaaaaaat | gctgaatctc | atcagtaatc aggaaaatgc | 3720 |
| aggttaaaac | aataccattt | ttcacccatc | agcttagcaa | aaatgagtat atttttaac | 3780 |
| aagtgttggt | aaggatgtgg | aaatgtgagg | ttcttgtagt | aagaatgcaa atggcactct | 3840 |
| ttgtagagta | agtctgttga | catctcataa | aactgaaaat | gcacacaacc ctgtaaatct | 3900 |
| agcaactgca | ctcagttgat | ttcagcccat | acatacaaag | agacctgcat aagaatgtta | 3960 |
| ctaggctttg | taaaagcaaa | aaataaggaa | caacttaaac | atcatcagaa ggggaactga | 4020 |
| taaactctgg | tgtaatccat | accacagaaa | tacaacaccg | catgtacagg aatgtgctac | 4080 |
| atctatacaa | ataaatggtc | aaactcaaaa | aaaaaaaaaa | aa | 4122 |

<210> SEQ ID NO 7
<211> LENGTH: 4065
<212> TYPE: DNA
<213> ORGANISM: Homo sapiens

<400> SEQUENCE: 7

| | | | | |
|---|---|---|---|---|
| gcgagcgaag | ggagcgctct | gggatgggac | ttggagcaag | cggcggcggc ggagacagag | 60 |
| gcagaggcag | aagctggggc | tccgtcctcg | cctcccacga | gcgatccccg aggagagccg | 120 |
| cggccctcgg | cgaggcgaag | aggccgacga | ggaagacccg | ggtggctgcg ccctgcctc | 180 |
| gcttccagg | cgccggcggc | tgcagccttg | cccctcttgc | tcgccttgaa aatggaaaag | 240 |
| atgctcgcag | gctgctttct | gctgatcctc | ggacagatcg | tcctcctccc tgccgaggcc | 300 |
| agggagcggt | cacgtgggag | gtccatctct | aggggcagac | acgctcggac ccacccgcag | 360 |
| acggcccttc | tggagagttc | ctgtgagaac | aagcgggcag | acctggtttt catcattgac | 420 |
| agctctcgca | gtgtcaacac | ccatgactat | gcaaaggtca | aggagttcat cgtggacatc | 480 |
| ttgcaattct | tggacattgg | tcctgatgtc | acccgagtgg | gcctgctcca atatggcagc | 540 |
| actgtcaaga | atgagttctc | cctcaagacc | ttcaagagga | agtccgaggt ggagcgtgct | 600 |
| gtcaagagga | tgcggcatct | gtccacgggc | accatgactg | gctgccat ccagtatgcc | 660 |
| ctgaacatcg | cattctcaga | agcagagggg | gcccggcccc | tgagggagaa tgtgccacgg | 720 |
| gtcataatga | tcgtgacaga | tgggagacct | caggactccg | tggccgaggt ggctgctaag | 780 |
| gcacgggaca | cgggcatcct | aatctttgcc | attggtgtgg | gccaggtaga cttcaacacc | 840 |
| ttgaagtcca | ttgggagtga | gccccatgag | gaccatgtct | tccttgtggc caatttcagc | 900 |
| cagattgaga | cgctgacctc | cgtgttccag | aagaagttgt | gcacggccca catgtgcagc | 960 |
| accctggagc | ataactgtgc | ccacttctgc | atcaacatcc | ctggctcata cgtctgcagg | 1020 |
| tgcaaacaag | gctacattct | caactcggat | cagacgactt | gcagaatcca ggatctgtgt | 1080 |
| gccatggagg | accacaactg | tgagcagctc | tgtgtgaatg | tgccgggctc cttcgtctgc | 1140 |

```
cagtgctaca gtggctacgc cctggctgag gatgggaaga ggtgtgtggc tgtggactac      1200
tgtgcctcag aaaaccacgg atgtgaacat gagtgtgtaa atgctgatgg ctcctacctt      1260
tgccagtgcc atgaaggatt tgctcttaac ccagataaaa aaacgtgcac aaagatagac      1320
tactgtgcct catctaatca cggatgtcag cacgagtgtg ttaacacaga tgattcctat      1380
tcctgccact gcctgaaagg ctttaccctg aatccagata agaaaacctg cagaaggatc      1440
aactactgtg cactgaacaa accgggctgt gagcatgagt gcgtcaacat ggaggagagc      1500
tactactgcc gctgccaccg tggctacact ctggacccca atggcaaaac ctgcagccga      1560
gtggaccact gtgcacagca ggaccatggc tgtgagcagc tgtgtctgaa cacggaggat      1620
tccttcgtct gccagtgctc agaaggcttc ctcatcaacg aggacctcaa gacctgctcc      1680
cgggtggatt actgcctgct gagtgaccat ggttgtgaat actcctgtgt caacatggac      1740
agatcctttg cctgtcagtg tcctgaggga cacgtgctcc gcagcgatgg gaagacgtgt      1800
gcaaaattgg actcttgtgc tctggggac cacggttgtg aacattcgtg tgtaagcagt      1860
gaagattcgt ttgtgtgcca gtgctttgaa ggttatatac tccgtgaaga tggaaaaacc      1920
tgcagaagga agatgtctg ccaagctata gaccatggct gtgaacacat ttgtgtgaac      1980
agtgatgact catacacgtg cgagtgcttg gagggattcc ggctcgctga ggatgggaaa      2040
cgctgccgaa ggaaggatgt ctgcaaatca acccaccatg gctgcgaaca catttgtgtt      2100
aataatggga attcctacat ctgcaaatgc tcagagggat ttgttctagc tgaggacgga      2160
agacggtgca gaaatgcac tgaaggccca attgacctgg tctttgtgat cgatggatcc      2220
aagagtcttg gagaagagaa ttttgaggtc gtgaagcagt ttgtcactgg aattatagat      2280
tccttgacaa tttcccccaa agccgctcga gtggggctgc tccagtattc cacacaggtc      2340
cacacagagt tcactctgag aaacttcaac tcagccaaag acatgaaaaa agccgtggcc      2400
cacatgaaat acatgggaaa gggctctatg actgggctgg ccctgaaaca catgtttgag      2460
agaagtttta cccaaggaga aggggccagg cccctttcca aagggtgcc cagagcagcc      2520 attgtgttca ccgacggacg ggctcaggat gacgtctccg agtgggccag taaagccaag      2580
gccaatggta tcactatgta tgctgttggg gtaggaaaag ccattgagga ggaactacaa      2640
gagattgcct ctgagcccac aaacaagcat ctcttctatg ccgaagactt cagcacaatg      2700
gatgagataa gtgaaaaact caagaaaggc atctgtgaag ctctagaaga ctccgatgga      2760
agacaggact ctccagcagg ggaactgcca aaaacggtcc aacagccaac agtgcaacac      2820
agatatctgt ttgaagaaga caatcttta cggtctacac aaaagctttc ccattcaaca      2880
aaaccttcag gaagcccttt ggaagaaaaa cacgatcaat gcaaatgtga aaaccttata      2940
atgttccaga accttgcaaa cgaagaagta agaaaattaa cacagcgctt agaagaaatg      3000
acacagagaa tggaagccct ggaaaatcgc ctgagataca gatgaagatt agaaatcgcg      3060
acacatttgt agtcattgta tcacggatta caatgaacgc agtgcagagc cccaaagctc      3120
aggctattgt taaatcaata atgttgtgaa gtaaaacaat cagtactgag aaacctggtt      3180
tgccacagaa caaagacaag aagtatacac taacttgtat aaatttatct aggaaaaaaa      3240
tccttcagaa ttctaagatg aatttaccag gtgagaatga ataagctatg caaggtatttt     3300 tgtaatatac tgtggacaca acttgcttct gcctcatcct gccttagtgt gcaatctcat      3360
ttgactatac gataaagttt gcacagtctt acttctgtag aacactggcc ataggaaatg      3420 ctgtttttt gtactggact ttaccttgat atatgtatat ggatgtatgc ataaaatcat      3480
aggacatatg tacttgtgga acaagttgga ttttttatac aatattaaaa ttcaccactt      3540
```

| | |
|---|---|
| cagagaatgg tattcagtgc aaaaattctt agtttaactt taaatggaag atatgtatgt | 3600 |
| atgagaaatg gccaacatgc ctatgaaaaa aatgctgaat ctcatcagta atcaggaaaa | 3660 |
| tgcaggttaa aacaatacca tttttcaccc atcagcttag caaaaatgag tatatttttt | 3720 |
| aacaagtgtt ggtaaggatg tggaaatgtg aggttcttgt agtaagaatg caaatggcac | 3780 |
| tctttgtaga gtaagtctgt tgacatctca taaaactgaa aatgcacaca accctgtaaa | 3840 |
| tctagcaact gcactcagtt gatttcagcc catacataca aagagacctg cataagaatg | 3900 |
| ttactaggct ttgtaaaagc aaaaaataag gaacaactta aacatcatca gaagggaac | 3960 |
| tgataaactc tggtgtaatc cataccacag aaatacaaca ccgcatgtac aggaatgtgc | 4020 |
| tacatctata caaataaatg gtcaaactca aaaaaaaaaa aaaaa | 4065 |

<210> SEQ ID NO 8
<211> LENGTH: 2600
<212> TYPE: DNA
<213> ORGANISM: Homo sapiens

<400> SEQUENCE: 8

| | |
|---|---|
| aaatccgagc ctcgcgtggg ctcctggccc ccgacggaca ccaccaggcc cacggagccc | 60 |
| accatgccgc gcccggcccc cgcgcgccgc ctcccgggac tcctcctgct gctctggccg | 120 |
| ctgctgctgc tgccctccgc cgccccgac cccgtggccc gccgggctt ccggaggctg | 180 |
| gagacccgag gtcccggggg cagccctgga cgccgcccct ctcctgcggc tcccgacggc | 240 |
| gcgcccgctt ccgggaccag cgagcctggc cgcgcccgcg gtgcaggtgt ttgcaagagc | 300 |
| agacccttgg acctggtgtt tatcattgat agttctcgta gcgtacggcc cctggaattc | 360 |
| accaaagtga aaacttttgt ctcccggata atcgacactc tggacattgg gccagccgac | 420 |
| acgcgggtgg cagtggtgaa ctatgctagc actgtgaaga tcgagttcca actccaggcc | 480 |
| tacacagata agcagtccct gaagcaggcc gtgggtcgaa tcacacccct tgtcaacagg | 540 |
| accatgtcag gcctagccat ccagacagca atggacgaag ccttcacagt ggaggcaggg | 600 |
| gctcgagagc cctcttctaa catccctaag gtggccatca ttgttacaga tgggaggccc | 660 |
| caggaccagg tgaatgaggt ggcggctcgg gcccaagcat ctggtattga gctctatgct | 720 |
| gtgggcgtgg accgggcaga catggcgtcc ctcaagatga tggccagtga gcccctagag | 780 |
| gagcatgttt tctacgtgga gacctatggg gtcattgaga aactttcctc tagattccag | 840 |
| gaaaccttct gtgcgctgga cccctgtgtg cttggaacac accagtgcca gcacgtctgc | 900 |
| atcagtgatg gggaaggcaa gcaccactgt gagtgtagcc aaggatacac cttgaatgcc | 960 |
| gacaagaaaa cgtgttcagc tcttgatagg tgtgctctta acacccacgg atgtgagcac | 1020 |
| atctgtgtga atgacagaag tggctcttat cattgtgagt gctatgaagg ttataccttg | 1080 |
| aatgaagaca ggaaaacttg ttcagctcaa gataaatgtg ctttgggtac ccatgggtgt | 1140 |
| cagcacattt gtgtgaatga cagaacaggg tccatcatt gtgaatgcta tgagggctac | 1200 |
| actctgaatg cagataaaaa aacatgttca gtccgtgaca agtgtgccct aggctctcat | 1260 |
| ggttgccagc acatttgtgt gagtgatggg ccgcatcct accactgtga ttgctatcct | 1320 |
| ggctacacct taaatgagga caagaaaaca tgttcagcca ctgaggaagc acgaagactt | 1380 |
| gtttccactg aagatgcttg tggatgtgaa gctacactgg cattccagga caaggtcagc | 1440 |
| tcgtatcttc aaagactgaa cactaaactt gatgacattt tggagaagtt gaaaataaat | 1500 |
| gaatatggac aaatacatcg ttaaattgct ccaatttctc acctgaaaat gtggacagct | 1560 |

-continued

| | |
|---|---|
| tggtgtactt aatactcatg cattcttttg cacacctgtt attgccaatg ttcctgctaa | 1620 |
| taatttgcca ttatctgtat taatgcttga atattactgg ataaattgta tgaagatctt | 1680 |
| ctgcagaatc agcatgattc ttccaaggaa atacatatgc agatacttat taagagcaaa | 1740 |
| ctttagtgtc tctaagttat gactgtgaaa tgattggtag gaaatagaat gaaaagttta | 1800 |
| gtgtttcttt atctactaat tgagccattt aattttttaaa tgtttatatt agataaccat | 1860 |
| attcacaatg gaaactttag gtctagtttc ttttgatagt atttataata taaatcaatc | 1920 |
| ttattactga gagtgcaaat tgtacaaggt atttacacat acaacttcat ataactgaga | 1980 |
| tgaatgtaat tttgaactgt ttaacacttt tgttttttg cttatttgt tggagtatta | 2040 |
| ttgaagatgt gatcaataga ttgtaataca catatctaaa aatagttaac acagatcaag | 2100 |
| tgaacattac attgccattt ttaattcatt ctggtctttg aaagaaatgt actactaaag | 2160 |
| agcactagtt gtgaatttag ggtgttaaac ttttaccaa gtacaaaaat cccaaattca | 2220 |
| ctttattatt ttgcttcagg atccaagtga caaagttata tatttataaa attgctataa | 2280 |
| atcgacaaaa tctaatgttg tctttttaat gttagtgatc cacctgcctc agcctcccaa | 2340 |
| agtgctggga ttacaggctt gaaagtctaa cttttttta cttatatatt tgatacatat | 2400 |
| aattcttttg gctttgaaac ttgcaacttt gagaacaaaa cagtccttta aattttgcac | 2460 |
| tgctcaattc tgttttcgt ttgcattgtc tttaatataa taaaagttat tacctttaca | 2520 |
| tattatcatg tctattttg atgactcatc aattttgtct attaaagata tttctttaaa | 2580 |
| ttaaaaaaaa aaaaaaaaa | 2600 |

<210> SEQ ID NO 9
<211> LENGTH: 2270
<212> TYPE: DNA
<213> ORGANISM: Homo sapiens

<400> SEQUENCE: 9

| | |
|---|---|
| aaatgcggcc gttgcctctg tgtgctccag ctgcctggca gtccccacct agggcacgct | 60 |
| gccacgccgc cgttacctgg tccaagtgcc cgggaggctc cgcctgtcgg cttcgctctg | 120 |
| cagctgcatc tctgatctgt cctgcaggct caggctctga cacctccatt ctctgtcccc | 180 |
| aagcgccatg agaggccttc tttgctggcc cgtgttgctg ctccttcttc agccctggga | 240 |
| aacccagctc cagttgacag gtcccaggtg tcacactggg ccctggatc tggtgttcgt | 300 |
| gattgacagc tcccgcagcg tgcgcccttt cgagttcgag accatgcggc agttcctcat | 360 |
| gggcctcctc cgaggcctga acgtgggtcc caacgccacg cgcgttggcg tgatccagta | 420 |
| ttcgagtcaa gtgcagagcg tcttccctct ccgcgcgttc tctcgccgcg aggacatgga | 480 |
| gcgcgccatc cgcgacctgg tgcctctggc gcaaggcacc atgacgggac tggcaatcca | 540 |
| gtacgccatg aacgtggcct tcagtgtggc cgagggcgcg cgaccgccag aggagcgcgt | 600 |
| gccgcgtgtc gctgtcatcg tgacagacgg gcggccccag gaccgcgtgg ccagggtggc | 660 |
| ggcacaggcg cgcgcccgcg gcattgaaat ttacgcggtg ggggtgcagc gcgcggacgt | 720 |
| gggctcccct gcgcgccatg catcgccccc gctagacgag cacgtcttcc tcgtagagtc | 780 |
| cttcgacctc atccaggagt tcggcctgca gttccagagc cggctgtgtg ccattgatct | 840 |
| gtgtgctgaa gggacccatg gatgtgagca ccactgcgtc aattccccag ctcctatttt | 900 |
| ctgtcactgc caagttggct ttgtactcca gcaggaccag aggagctgca gggccattga | 960 |
| ctactgcagc tttgggaacc atagctgtca gcatgagtgt gttagcaccc tggtggcc | 1020 |
| acggtgccac tgcagagagg gccatgactt gcagcctgat ggggaggagct gtcaggtccg | 1080 |

| | |
|---|---|
| ggacctttgc aatggcgtgg accatggctg tgagttccag tgtgtgagcg agggcctctc | 1140 |
| ctaccgctgc ctgtgccccg aggggcggca acttcaggca gatggcaaga gctgcaaccg | 1200 |
| gtgccgggaa ggccacgtgg accttgttct gctggttgat ggctccaaga gcgtgcgtcc | 1260 |
| acaaaacttc gagctagtga agcgcttcgt gaaccagatt gtggacttcc tagatgtgtc | 1320 |
| ccccgagggc acgcgggtgg ggctggtgca gttctcgagc cgcgtgcgca ccgagttccc | 1380 |
| tctgggtcgc tacggcaccg cagccgaggt gaagcaggcg gtcctggccg tggagtacat | 1440 |
| ggaacgcggc accatgacag ggctggcgtt gcggcacatg gtggagcaca gcttctccga | 1500 |
| ggcgcagggt gcacggcccc gtgcccttaa cgtgcctcgt gttggcctgg tcttcacgga | 1560 |
| tggccgctcc caggatgaca tctcggtgtg gcagcgcgc gccaaggagg aaggcatcgt | 1620 |
| catgtacgcc gtgggcgtgg gcaaggcggt ggaggcggag ctgcgcgaga tcgcctcgga | 1680 |
| gccagcggaa ctgcacgtgt cctatgcccc ggacttcggc accatgacgc acctgctgga | 1740 |
| gaacctcaga ggcagcatct gtccagagga gggcatcagc gcaggacag agcttcggag | 1800 |
| cccatgcgaa tgcgaaagcc tcgtggagtt ccagggccgc acgctggggg cgctcgagag | 1860 |
| cctgacgctg aacctggccc agctgacggc gcgcctggag gatctggaga accagctggc | 1920 |
| caaccagaag tgagggccac ggacggccca gacccgggct ggggcgcggc accacggacg | 1980 |
| gtgcccttg cgcgccatcg gtgcgccggg gccaggcaga acctgggccc gtccggcttg | 2040 |
| ggctgtcggg gcggaggcgc tggcgggctt ccggcattga gctgagttgg cctcgcccgg | 2100 |
| accattaggc ggactgcggc gtcaggggga tagcgggtgg tgagggaagg ggcacgtgct | 2160 |
| agaccggcac gccctcgccg cgtgctgcgc tcagttcttt gttggattc ttgtttgtgt | 2220 |
| tcttaaaaaa ataaaaaaaa ctgatttcca cggaaaaaaa aaaaaaaaa | 2270 |

<210> SEQ ID NO 10
<211> LENGTH: 2147
<212> TYPE: DNA
<213> ORGANISM: Homo sapiens

<400> SEQUENCE: 10

| | |
|---|---|
| aaatgcggcc gttgcctctg tgtgctccag ctgcctggca gtccccacct agggcacgct | 60 |
| gccacgccgc cgttacctgg tccaagtgcc cgggaggctc cgcctgtcgg cttcgctctg | 120 |
| cagctgcatc tctgatctgt cctgcaggct caggctctga cacctccatt ctctgtcccc | 180 |
| aagcgccatg agaggccttc tttgctggcc cgtgttgctg ctccttcttc agccctggga | 240 |
| aacccagctc cagttgacag gtcccaggtg tcacactggg ccctggatc tggtgttcgt | 300 |
| gattgacagc tcccgcagcg tgcgcccttt cgagttcgag accatgcggc agttcctcat | 360 |
| gggcctcctc cgaggcctga acgtgggtcc caacgccacg cgcgttggcg tgatccagta | 420 |
| ttcgagtcaa gtgcagagcg tcttccctct ccgcgcgttc tctcgccgcg aggacatgga | 480 |
| gcgcgccatc cgcgacctgg tgcctctggc gcaaggcacc atgacgggac tggcaatcca | 540 |
| gtacgccatg aacgtggcct tcagtgtggc cgagggcgcg cgaccgccag aggagcgcgt | 600 |
| gccgcgtgtc gctgtcatcg tgacagacgg gcggccccag gaccgcgtgg ccgaggtggc | 660 |
| ggcacaggcg cgcgcccgcg gcattgaaat ttacgcggtg ggggtgcagc gcgcggacgt | 720 |
| gggctccctg cgcgccatgg catcgccccc gctagacgag cacgtcttcc tcgtagagtc | 780 |
| cttcgacctc atccaggagt tcggcctgca gttccagagc cggctgtgtg ccattgacta | 840 |
| ctgcagcttt gggaaccata gctgtcagca tgagtgtgtt agcaccctg gtgggccacg | 900 |

```
gtgccactgc agagagggcc atgacttgca gcctgatggg aggagctgtc aggtccggga    960
cctttgcaat ggcgtggacc atggctgtga gttccagtgt gtgagcgagg gcctctccta   1020
ccgctgcctg tgccccgagg ggcggcaact tcaggcagat ggcaagagct gcaaccggtg   1080
ccgggaaggc cacgtggacc ttgttctgct ggttgatggc tccaagagcg tgcgtccaca   1140
aaacttcgag ctagtgaagc gcttcgtgaa ccagattgtg gacttcctag atgtgtcccc   1200
cgagggcacg cgggtggggc tggtgcagtt ctcgagccgc gtgcgcaccg agttccctct   1260
gggtcgctac ggcaccgcag ccgaggtgaa gcaggcggtc ctggccgtgg agtacatgga   1320
acgcggcacc atgacagggc tggcgttgcg cacatggtg gagcacagct tctccgaggc    1380
gcagggtgca cggccccgtg cccttaacgt gcctcgtgtt ggcctggtct tcacggatgg   1440
ccgctcccag gatgacatct cggtgtgggc agcgcgcgcc aaggaggaag gcatcgtcat   1500
gtacgccgtg ggcgtgggca aggcggtgga ggcggagctg cgcgagatcg cctcggagcc   1560
agcggaactg cacgtgtcct atgccccgga cttcggcacc atgacgcacc tgctggagaa   1620
cctcagaggc agcatctgtc cagaggaggg catcagcgca gggacagagc ttcggagccc   1680
atgcgaatgc gaaagcctcg tggagttcca gggccgcacg ctgggggcgc tcgagagcct   1740
gacgctgaac ctggcccagc tgacggcgcg cctggaggat ctggagaacc agctggccaa   1800
ccagaagtga gggccacgga cggcccagac ccgggctggg gcgcggcacc acggacggtg   1860 cccccttgcgc gccatcggtg cgccggggcc aggcagaacc tgggcccgtc cggcttgggc   1920
tgtcggggcg gaggcgctgg cgggcttccg gcattgagct gagttggcct cgcccggacc   1980
attaggcgga ctgcggcgtc aggggatag cgggtggtga gggaaggggc acgtgctaga    2040
ccggcacgcc ctcgccgcgt gctgcgctca gttctttgtt ggatttcttg tttgtgttct   2100
taaaaaaata aaaaaactg atttccacgg aaaaaaaaaa aaaaaaa                  2147
```

<210> SEQ ID NO 11
<211> LENGTH: 2024
<212> TYPE: DNA
<213> ORGANISM: Homo sapiens

<400> SEQUENCE: 11

```
aaatgcggcc gttgcctctg tgtgctccag ctgcctggca gtccccacct agggcacgct     60
gccacgccgc cgttacctgg tccaagtgcc cgggaggctc cgcctgtcgg cttcgctctg    120
cagctgcatc tctgatctgt cctgcaggct caggctctga cacctccatt ctctgtcccc    180
aagcgccatg agaggcctt tttgctggcc cgtgttgctg ctccttcttc agccctggga    240
aacccagctc cagttgacag gtcccaggtg tcacactggg ccctggatc tggtgttcgt     300 gattgacagc tcccgcagcg tgcgcccttt cgagttcgag accatgcggc agttcctcat    360
gggcctcctc cgaggcctga acgtgggtcc caacgccacg cgcgttggcg tgatccagta    420
ttcgagtcaa gtgcagagcg tcttccctct ccgcgcgttc tctcgccgcg aggacatgga    480
gcgcgccatc cgcgacctgg tgcctctggc gcaaggcacc atgacgggac tggcaatcca    540
gtacgccatg aacgtggcct tcagtgtggc cgagggcgcg cgaccgccag aggagcgcgt    600
gccgcgtgtc gctgtcatcg tgacagacgg cggccccag gaccgcgtgg ccgaggtggc     660
ggcacaggcg cgcgcccgcg gcattgaaat ttacgcggtg ggggtgcagc gcgcggacgt    720
gggctccctg cgcgccatgg catcgccccc gctagacgag cacgtcttcc tcgtagagtc    780
cttcgacctc atccaggagt tcggcctgca gttccagagc cggctgtgtg tccgggacct    840
ttgcaatggc gtggaccatg gctgtgagtt ccagtgtgtg agcgagggcc tctcctaccg    900
```

```
ctgcctgtgc cccgaggggc ggcaacttca ggcagatggc aagagctgca accggtgccg    960
ggaaggccac gtggaccttg ttctgctggt tgatggctcc aagagcgtgc gtccacaaaa   1020
cttcgagcta gtgaagcgct tcgtgaacca gattgtggac ttcctagatg tgtccccga   1080 gggcacgcgg gtggggctgg tgcagttctc gagccgcgtg cgcaccgagt tccctctggg   1140
tcgctacggc accgcagccg aggtgaagca ggcggtcctg gccgtggagt acatggaacg   1200
cggcaccatg acagggctgg cgttgcggca catggtggag cacagcttct ccgaggcgca   1260
gggtgcacgg ccccgtgccc ttaacgtgcc tcgtgttggc ctggtcttca cggatggccg   1320
ctcccaggat gacatctcgg tgtgggcagc gcgcgccaag gaggaaggca tcgtcatgta   1380
cgccgtgggc gtgggcaagg cggtggaggc ggagctgcgc gagatcgcct cggagccagc   1440
ggaactgcac gtgtcctatg ccccggactt cggcaccatg acgcacctgc tggagaacct   1500
cagaggcagc atctgtccag aggagggcat cagcgcaggg acagagcttc ggagcccatg   1560
cgaatgcgaa agcctcgtgg agttccaggg ccgcacgctg ggggcgctcg agagcctgac   1620
gctgaacctg gcccagctga cggcgcgcct ggaggatctg gagaaccagc tggccaacca   1680
gaagtgaggg ccacggacgg cccagacccg ggctggggcg cggcaccacg gacggtgccc   1740
cttgcgcgcc atcggtgcgc cggggccagg cagaacctgg gcccgtccgg cttgggctgt   1800
cggggcggag gcgctggcgg gcttccggca ttgagctgag ttggcctcgc ccggaccatt   1860
aggcggactg cggcgtcagg gggatagcgg gtggtgaggg aaggggcacg tgctagaccg   1920
gcacgccctc gccgcgtgct gcgctcagtt ctttgttgga tttcttgttt gtgttcttaa   1980
aaaaataaaa aaaactgatt tccacggaaa aaaaaaaaaa aaaa               2024
```

COMPOSITIONS AND METHODS FOR THE TREATMENT OF ORTHOPEDIC DISEASE OR INJURY

RELATED APPLICATIONS

This application is a national stage application, filed under 35 U.S.C. § 371, of International Application No. PCT/US2012/020353 filed Jan. 5, 2012, which claims the benefit of U.S. Provisional Application No. 61/430,134 filed Jan. 5, 2011, the contents of each of which are incorporated by reference in their entireties.

ACKNOWLEDGEMENT OF GOVERNMENT SUPPORT

This invention was made with Government support awarded by the National Institute on Aging of the National Institutes of Health, under Grant No. AG014399. The Government has certain rights to this invention.

FIELD OF THE DISCLOSURE

The present invention relates to compositions and methods for the treatment of cartilage joint injury or diseases including osteoarthritis.

INCORPORATION-BY-REFERENCE OF SEQUENCE LISTING

The contents of the text file named "21486_597N01US_ST25.txt", which was created on Jun. 7, 2015, and is 11.1 KB in size, are hereby incorporated by reference in their entirety.

BACKGROUND OF THE DISCLOSURE

Osteoarthritis (OA) is characterized by its degenerative effect on major extracellular matrix (ECM) components such as type II collagen and aggrecan in articular cartilage. This enhancement of articular cartilage ECM catabolism is largely mediated by the matrix metalloproteinase (MMP) family of collagenases and the ADAMTS family of aggrecanases. Furthermore, increase of the concentration of inflammatory cytokines such as IL-1β, which occurs during OA pathogenesis, often leads to repression of synthesis of type II collagen and aggrecan, and upregulation of MMP13 and ADAMTS-4 and -5, thereby favoring cartilage degeneration.

Matrilin-3 (MATN3) is a member of the non-collagenous matrilin family of ECM proteins that share common domains and similar functions. While MATN1 and MATN3 are distributed specifically in cartilage, MATN2 and MATN4 are distributed in many connective tissues. Mutation of MATN3 results in a variety of skeletal diseases including chondrodysplasia and osteoarthritis. MATN3 KO mice exhibit relatively normal skeletal development but develop accelerated articular cartilage degeneration during aging. However, the mechanism by which MATN3 acts chondroprotectively is yet unknown and traditionally it was believed that the role of MATN3 is purely structural as an ECM protein.

SUMMARY OF THE DISCLOSURE

The compositions and methods described herein provide a solution to the drawbacks and problems associated with earlier clinical approaches to treatment of articular joint injury or degeneration such as arthritis. Earlier methods did nothing more than alleviate symptoms, whereas the compositions and methods of the invention manipulate underlying mechanisms that lead to development of arthritis. The methods described herein utilize matrilin and derivatives or fragments thereof to protect and treat joint degeneration and inflammation, to repair or refill cartilage defects, and as a component of tissue engineered bioscaffolds and prosthetic devices.

Accordingly, a method for reducing the severity of an arthritic condition is carried out by administering to a subject suffering from or at risk of developing the condition a composition comprising a member of the matrilin family of proteins, e.g., purified matrilin or a fragment thereof, in an amount that reduces the severity of the condition. The composition is administered directly into or onto articulating joint or osteochondral tissue. An osteochondral tissue is one pertaining to or composed of bone or cartilage, or both bone and cartilage. For example, matrilin a matrilin-3 protein or fragment thereof or a matrilin-1 protein or fragment thereof. Exemplary articulating joints include a knee, hip, elbow, or shoulder. An exemplary osteochondral tissue comprises a vertebra. In preferred embodiments, the matrilin or fragment thereof is administered locally, e.g., by intra-articular injection rather than systemically, e.g., orally or intravenously. An advantage of local (versus systemic) administration of matrilin includes the avoidance of side effects such as immune complications that may be associated with systemic dissemination of the compound.

The invention also includes a method of repairing a cartilage defect, such as a defect caused by a traumatic injury, e.g., a sports injury, or by degenerating tissue. The method is carried out by administering to a subject suffering from said defect a composition comprising purified matrilin or a fragment thereof. As described above, the composition is preferably administered locally, e.g., directly into or onto the defect. The matrilin is a member of the matrilin family such as a matrilin-3 protein or fragment thereof or a matrilin-1 protein or fragment thereof. The cartilage defect is in an articulating joint or an osteochondral tissue. In preferred embodiments, the composition is injected to the affected site, e.g., by intra-articular injection.

Also within the invention is a gene therapy method for treatment of osteoarthritis by locally administering to an individual in need thereof a therapeutically effective amount of an expression vector. The vector comprises a promoter sequence capable of directing the expression of an operably linked polypeptide, which is a member of the matrilin family, e.g., the encoded polypeptide comprises a matrilin-3 polypeptide or a matrilin-1 polypeptide or a fragment thereof.

A pharmaceutical composition comprises a matrilin nucleic acid in a formulation suitable for intra-articular injection or a matrilin polypeptide in a formulation suitable for intra-articular injection. Optionally, other compounds or agents are present in the composition, e.g., a lubricating agent, e.g., hyaluronic acid or a tribonectin, or a corticosteroid. Exemplary matrilin compositions are liquid, gels, or pastes, e.g., packaged in vials for injection or pre-packaged in syringes for administration.

The invention also includes tissue engineered structures and devices that contain matrilin. Such structures and devices are used in place of or in conjunction with metal, e.g., titanium, devices currently used in joint replacement surgery. A prosthetic joint device comprising a biocomposite composition in the shape of a knee or hip component, wherein said composition comprises a matrilin protein or fragment.

Also within the invention is a method for reducing the severity of an arthritic condition comprising orally administering to a subject suffering from or at risk of developing the condition an edible composition comprising purified matrilin-3 or a fragment thereof in an amount that reduces the severity of the condition. Matrilin-3 is administered in an amount that reduces the severity of the condition, e.g., in an amount that reduces joint degeneration and/or inflammation. The composition optionally comprises a food or pharmaceutically-acceptable carrier. For example, it is in the form of a nutritional supplement, e.g., a liquid drink, capsule, tablet, gelcap, or powder. An exemplary oral dosage unit is 0.1-100 mg, e.g., 1-10 mg per day.

For local therapy, administration into a joint space is accomplished by arthroscopic manipulation or direct injection or infusion into the joint (intra-articular administration). The composition is also useful as a biologic glue or cement that is applied directly onto injured or diseased bone or cartilage tissue.

Also within the invention is a biomaterial such as a scaffold for tissue engineering or manufacture of artificial joints. Such a biomaterial comprises matrilin-3 or a fragment thereof as well as other chondroconductive or chondroinductive materials, e.g., other ECM proteins or biomimetic materials including nanomaterials.

The amount or dose of matrilin is one that attenuates arthritis symptoms or pathogenesis. For example, in the optimal concentration range of matrilin, it exerts a positive effect for cartilage protection e.g., by upregulating expression of endogenous IL-1β pathway inhibitor IL-1RA, upregulating Col II or aggrecan, and/or downregulating MMP-13, ADAMTS-4 or 5. For example, the dose/amount of matrilin-3 upregulates IL1-RA expression in treated tissues, inhibits expression of IL-1β pathway targets, and/or upregulates Type II collagen expression.

The compositions and methods are suitable for treating mammalian subjects such as those of the human, or an equine, canine, or feline species.

In a still further aspect the invention relates to use of the proteins, peptides, vectors, or tissue engineering constructs for the preparation of a medicament for the treatment of a joint disorder.

Furthermore, the invention relates to a method of treating a joint disease, said method comprising administering to an individual in need thereof: a therapeutically effective amount of the vector of the invention; or a therapeutically effective amount of the pharmaceutical composition of the invention.

According to some embodiments, there is provided in vivo gene therapy methods for the treatment of joint diseases. According to some embodiments, there is provided methods for treating joint disorders based on ex vivo gene therapy and implantation of therapeutic cells capable of secreting increased amounts of the Matrilin-3.

Figure 10:
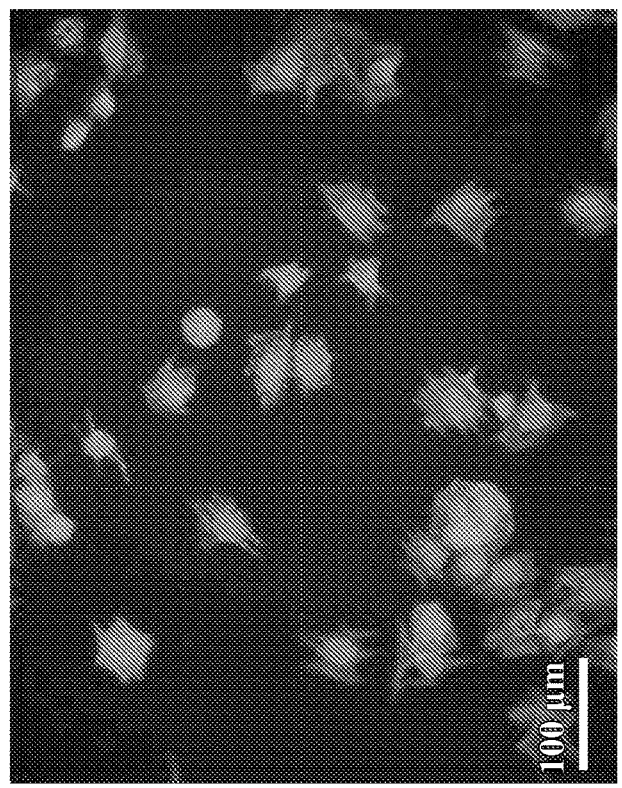
Figure 10:
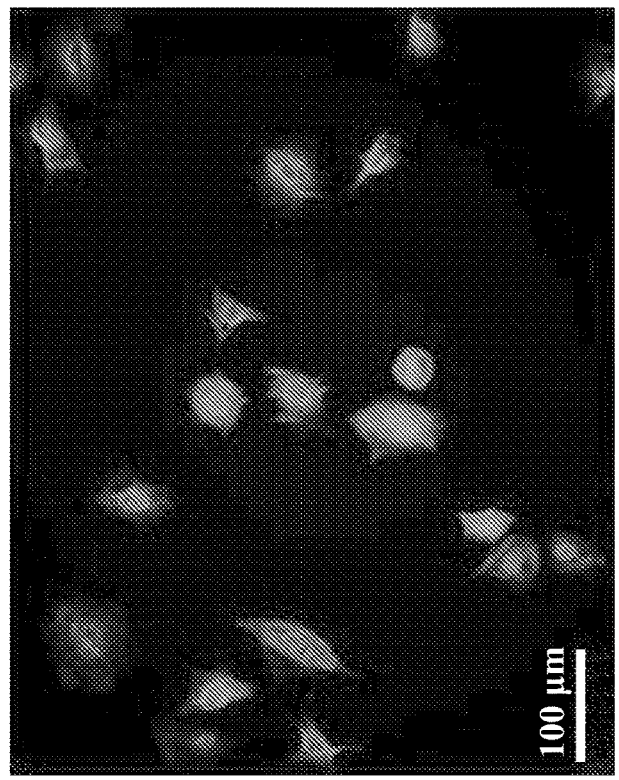

FIG. 10 is a series of photomicrographs. Chondrocyte morphology in monolayer cell culture in the absence (Right) and presence (Left) of recombinant human MATN3 protein. Cells bodies exhibited a wider and more spread-out morphology in the presence of MATN3 protein indicative of better cell-to-surface adhesion.

Figure 11A:
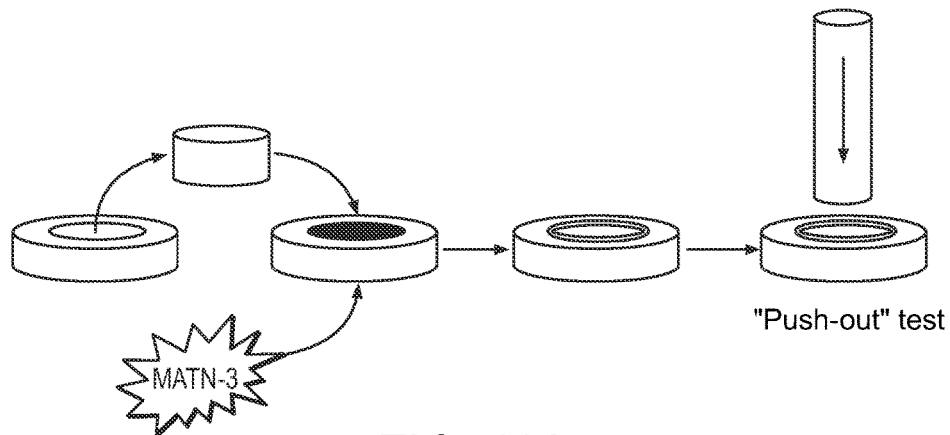
Figure 11B:
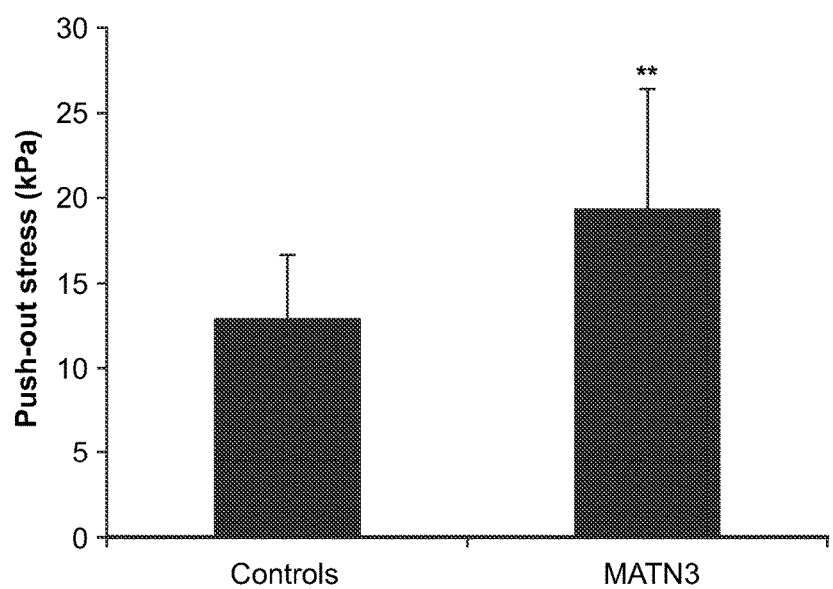

FIGS. 11A-B are a diagram and a bar graph, respectively. Diagram of the push-out test experiment designed to measure force required to dislodge a piece of cartilage tissue used to fill a cartilage defect (A). MATN3 enhanced the adhesion and integration of the defected cartilage tissue in mechanical push-out tests (B). Double asterisks ** indicates statistically significant differences of p≤0.01. Data are representative of at least 6 individual experiments.

Figure 12A:
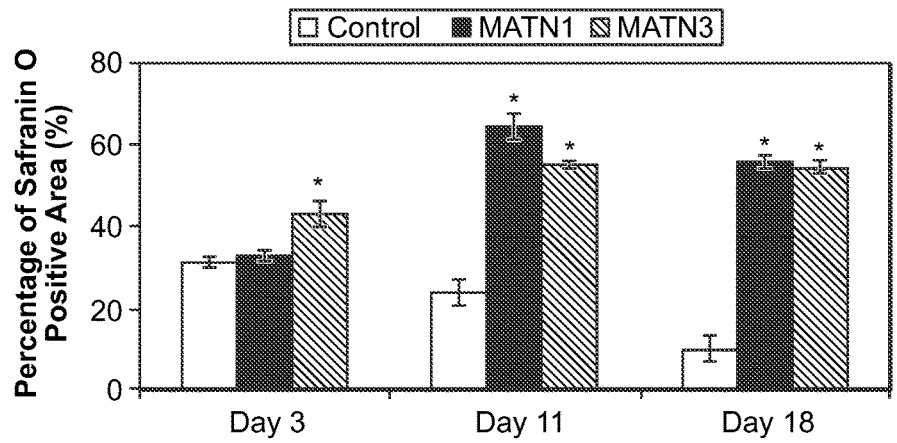
Figure 12B:
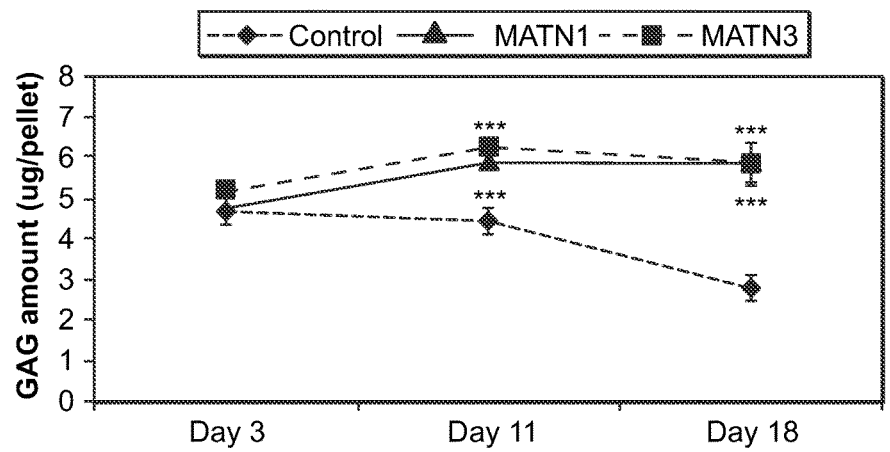
Figure 12C:
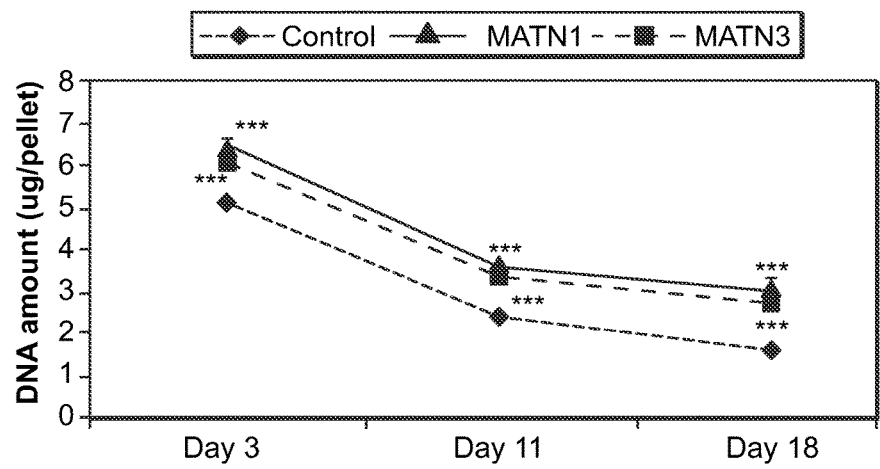

FIG. 12 A is a bar graph, and FIGS. 12B-C are line graphs. Enhancement of chondrogenesis (cartilage formation) by the expression of MATN1 or MATN3 in the pellet culture of mesenchymal stem cells from pig joint synovium. (A) Quantification of the percentage of safranin-O positive areas in SFB pellet sections.*Significantly higher than the corresponding control group,*P<0.05, P<0.01, and *P<0.001. Error bars represent the mean standard deviation (SD). (B) Compared to the control, expression of either MATN1 or MATN3 increased the amount of GAG within the SFB pellets at day 11 and day 18. (C) Expression of MATN1 or MATN3 and increased the DNA content (cell number) in the SFB pellets throughout the incubation period.*Significantly higher than the corresponding control group,*P<0.05, P<0.01, and *P<0.001. Error bars represent the mean SD.

Figure 13:
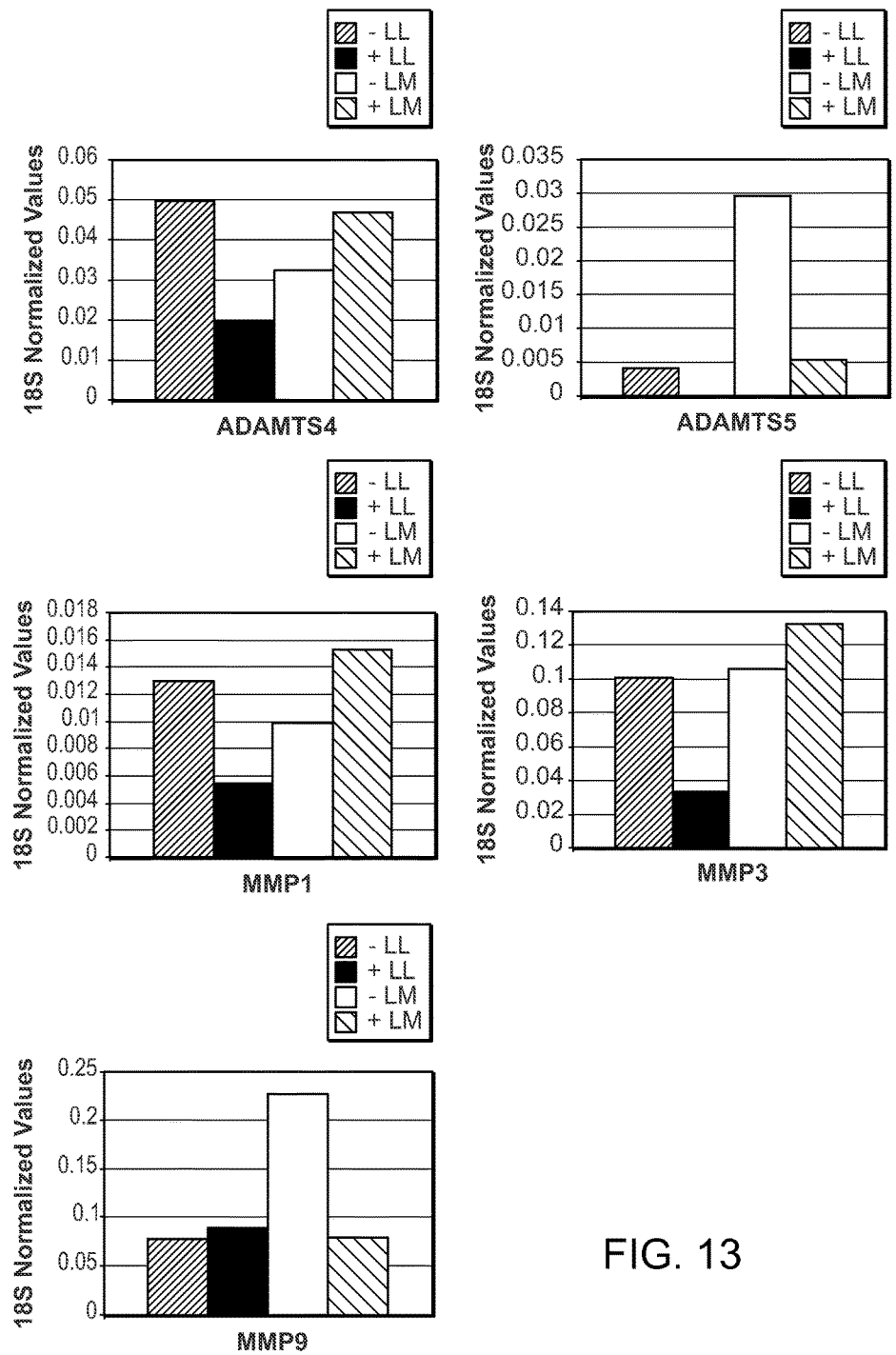

FIG. 13 is a series of bar graphs showing that intraarticular injection of recombinant matrilin-3 into a rabbit knee reduces the mRNA levels of catabolic matrix proteinases in articular cartilage during osteoarthritis (OA). OA was induced in the knee joint of young adult rabbit by transaction of ACL and PCL and removal of medial meniscus for 2 weeks before weekly injection of recombinant matrilin-3 (2 ml of 200 ng/ml) for 6 weeks. At Day 56, articular cartilage was harvested from experimental (matrilin treated) or control (saline treated) knees. mRNA was isolated and quantified by quantitative PCR with 18SRNA as internal control. −LL: Left knee joint lateral area (early osteoarthritis); without matrilin treatment (saline control). +LL: Left knee joint lateral area (early osteoarthritis); with matrilin treatment. −LM: Left knee joint medial area (late osteoarthritis); without matrilin treatment (saline control). −LM: Left knee joint medial area (late osteoarthritis); with matrilin treatment.

DETAILED DESCRIPTION OF THE INVENTION

Matrilin and fragments or derivatives thereof are useful as chondroprotective agents, e.g., to treat joint degeneration and inflammation. The invention is based on the discovery matrilin-3 protein has beneficial effects on cartilage cells by 1) enhancing their anabolism including stimulating the synthesis of major structural components of cartilage type II collagen) and aggrecan; 2) suppressing their catabolism including inhibiting synthesis of major matrix degradation enzymes such as matrix metalloproteinase 13 (MMP-13), ADAMTS-4 and ADAMTS-5; and 3) reducing inflammation including inhibiting proinflammatory cytokine interleukin-1 and its receptor IL1R and stimulating the synthesis of interleukin-1 receptor antagonist (IL-1Ra), which inhibits the effects of IL-1. For example, MATN3 upregulates gene expression of IL-RA both in the presence and in the absence of IL-1β; MATN3 inhibits IL-1β induced MMP-13 expression in a dose-dependant manner; MATN3 inhibits ADAMTS-4, -5 expression in a dose-dependant manner; MATN3 stimulates Col II expression; and MATN3 does not directly bind IL-1β. These activities are instrumental in conferring clinical benefit, and the compositions are administered such that one or more of these activities is demonstrated. Thus, matrilin-3 and its derived products protect against inflammation and joint cartilage degeneration by enhancing anabolism, and/or suppressing catabolism, and/or inhibiting pro-inflammatory pathways.

Members of the matrilin protein family, e.g., recombinant human MATN3 or MATN1, was found to enhance chondrogenic gene expression and protein level in chondrocytes and/or inhibiting the release of joint degrading catabolic proteases that are downstream of the interleukin-1 cytokine pathway. MATN3 stimulated the release of the anti inflammatory molecule; Interleukin-1 receptor antagonist (IL-1Ra). The data described herein indicates that MATN3 is useful as a therapeutic composition (e.g., via intra articular injection) for treatment of joint inflammation.

Furthermore, in addition to its chondrogenic and anti inflammatory properties, MATN3 was found to enhance chondrocyte cell-to-cell adhesion as well as cartilage whole tissue-to-tissue adhesion and stabilization. Based on these properties, MATN3 and other members of the matrilin family, e.g., MATN1, are useful therapeutic molecules for the purpose of repairing/refilling cartilage defects in injured patients.

Currently there are no FDA approved drugs specific for the treatment of OA. Existing therapies are only interventions for alleviating OA symptoms, e.g., (1) supplements that attempt to enhance the body's endogenous cartilage regenerative capabilities; (2) drugs that attempt to reduce OA associated pain; or (3) surgical interventions which replace the joint as the last resort.

In contrast to these existing approaches, the compositions and methods described herein intervene at the level of the actual cause of joint degeneration.

Although a role of the human MATN3 gene in osteoarthritis has been described (U.S. Publication No. 2003/0203380), Matrilin has never been used or described as either supplement or medicine for protecting against and treating inflammation and joint degeneration, and the activities of matrilin-3 described above were not known prior to the invention. Thus according to the invention, matrilin-3 is administered in a manner and at a dose that suppresses joint degeneration by inhibiting the expression of several major matrix proteases and pro-inflammatory pathways and/or promoting cartilage healing by enhancing the endogenous expression of major cartilage constituents (type II collagen, aggrecan).

Matrilins, active fragments, and derived products thereof are therefore useful as orally-ingested supplements to protect joint inflammation or degeneration, or as a injectable, infusible, or surface-applied (bone or cartilage surfaces) pharmacological treatment for orthopedic conditions and articular joint injury including OA and/or Rheumatoid Arthritis (RA), and other inflammatory degenerative diseases. The proteins, fragments, or derivatives are also useful as a biomaterials (e.g., scaffolds or biological glue/cement formulations) for repair of tissues such as cartilage or other tissues due to their anabolic enhancing, catabolic suppressing, and inflammation inhibiting properties. Active fragments include those that contain a vWFA domain, an EGF-like domain, and/or an alpha-helix domain (see, e.g., 1:

Fresquet et al., 2007, J Biol Chem. 2007 Nov. 30; 282(48): 34634-43. Epub 2007 Sep. 18. PubMed PMID: 17881354; PubMed Central PMCID: PMC2673055; or Klatt et al., 2000, J Biol Chem. 2000 Feb. 11; 275(6):3999-4006. PubMed PMID: 10660556; hereby incorporated by reference).

Members of the Matrilin Family

The following table describes the GenBank IDs for each of the matrilins as found on the NCBI database, the contents of each of the the Genbank citations below is hereby incorporated by reference. Two of the matrilins have multiple transcriptional variants.

| Gene | Species | GenBank mRNA Reference sequence |
|---|---|---|
| MATN1 | human | NM_002379.3 [SEQ ID NO: 5] |
| MATN2 | human | NM_002380.3 (Transcrip. Var. 1) [SEQ ID NO: 6] NM_030583.2 (Transcrip. Var. 2) [SEQ ID NO: 7] |
| MATN3 | human | NM_002381.4 [SEQ ID NO: 8] |
| MATN4 | human | NM_003833.3 (Transcrip. Var. 1) [SEQ ID NO: 9] NM_030590.2 (Transcrip. Var. 2) [SEQ ID NO: 10] NM_030592.2 (Transcrip. Var. 3) [SEQ ID NO: 11] |

Matrilin-3

Matrilin-3 is a protein that in humans is encoded by the MATN3 gene. Matrilin-3 is a 486 polypeptide having the following sequence (SEQ ID NO: 1).

```
Full MATN3 AA sequence: NCBI Reference Sequence: NP_002372.1
                                                     (SEQ ID NO: 1)
   1 mprpaparrl pgllllllwpl lllpsaapdp varpgfrrle trgpggspgr rpspaapdga
  61 pasqtsepgr argagvcksr pldlvfiids srsvrpleft kvktfvsrii dtldigpadt
 121 rvavvnyast vkiefqlqay tdkqslkgav gritplstgt msglaiqtam deaftveaga
 181 repssnipkv aiivtdgrpq dqvnevaara qasgielyav gvdradmasl kmmaseplee
 241 hvfyvetyqv ieklssrfqe tfcaldpcvl gthqcqhvci sdgegkhhce csqgytlnad
 301 kktcsaldrc alnthgcehi cvndrsgsyh cecyegytln edrktcsaqd kcalgthgcq
 361 hicvndrtgs hhcecyegyt lnadkktcsv rdkcalgshg cqhicvsdga asyhcdcypg
 421 ytlnedkktc sateearrlv stedacgcea tlafqdkvss ylqrlntkld dileklkine
 481 ygqihr MATN3 active domain sequence
        dp varpgfrrle trgpggspgr rpspaapdga pasgtsepgr argagvcksr
pldlvfiids srsvrpleft kvktfvsrii dtldigpadt rvavvnyast vkiefqlqay
tdkqslkgav gritplstgt msglaiqtam deaftveaga repssnipkv aiivtdgrpq
dqvnevaara qasgielyav gvdradmasl kmmaseplee hvfyvetyqv ieklssrfqe
tfcaldpcvl gthqcqhvci sdgegkhhce csqgytlnad kktcsaldrc alnthgcehi
cvndrsgsyh cecyegytln edrktcsaqd kcalgthgcq hicvndrtgs hhcecyegyt
lnadkktcsv rdkcalgshg cqhicvsdga asyhcdcypg ytlnedkktc sateearrlv
[corresponds to underlined sequence (above) of SEQ ID NO: 1]

MATN3 active domain sequence "hr"
                                                     (SEQ ID NO: 4)
        dp varpgfrrle trgpggspgr rpspaapdga pasgtsepgr argagvcksr
pldlvfiids srsvrpleft kvktfvsrii dtldigpadt rvavvnyast vkiefqlqay
tdkqslkgav gritplstgt msglaiqtam deaftveaga repssnipkv aiivtdgrpq
dqvnevaara qasgielyav gvdradmasl kmmaseplee hvfyvetyqv ieklssrfqe
tfcaldpcvl gthqcqhvci sdgegkhhce csqgytlnad kktcsaldrc alnthgcehi
cvndrsgsyh cecyegytln edrktcsaqd kcalgthgcq hicvndrtgs hhcecyegyt
lnadkktcsv rdkcalgshg cqhicvsdga asyhcdcypg ytlnedkktc sateearrlv hr
```

The MATN3 active domain sequence was determined by taking the full sequence and then taking away both the signaling peptide (mprpaparrl pgllllwpl lllpsaap of SEQ ID NO:1) and the ccoil domain (stedacgcea tlafqdkvss ylqrintkld dileklkine ygqihr of SEQ ID NO:1). Two exemplary active sequences are shown above. The active sequence "hr" contains the amino acids "hr" at the emd, because these two amino acids are not part of the ccoil domain.

```
Full MATN1 AA sequence: NCBI Reference Sequence: NP_002372.1
                                                     (SEQ ID NO: 3)
   1 wdegagqgwa gpldsghlcr trptdlvfvv dssrsvrpve fekvkvflsq viesldvgpn
  61 atrvgmvnya stvkqefslr ahvskaallq avrrigplst gtmtglaiqf aitkafgdae
 121 qgrsrspdis kvvivvtdgr pqdsvqdvsa rarasqvelf aiqvgsvdka tlrqiasepq
 181 dehvdyvesy svieklsrkf qeafcvvsdl catqdhdceq vcisspqsyt cacheqftln
 241 sdgktcnvcs ggggssatdl vflidgsksv rpenfelvkk fisqivdtld vsdklaqvgl
 301 vqyssvrqe fplgrfhtkk dikaavrnms ymekgtmtga alkylidnsf tvssgarpga
 361 qkvgivftdg rsqdyindaa kkakdlgfkm favgvgnave delreiasep vaehyfytad
 421 fktinqigkk lqkkicveed pcaceslvkf qakvegllqa ltrkleavsk rlailentvv
```

```
MATN1 active domain sequence
trptdlvfvv dssrsvrpve fekvkvflsq viesldvgpn atrvgmvnya stvkqefslr
ahvskaallq avrriqplst gtmtglaiqf aitkafgdae ggrsrspdis kvvivvtdgr
pqdsvqdvsa rarasgvelf aigvgsvdka tlrqiasepq dehvdyvesy svieklsrkf
qeafcvvsdl catgdhdceq vcisspgsyt cachegftln sdgkt
```
-continued Matrilin peptides (less than the full length naturally-occurring protein) are used in the methods. Useful peptides are those that comprise an activity of the full-length protein. The matrilin polypeptide contains amino acid sequences from one or more domains such as vWFA domain and the EGF-like domain. Some examples of the matrilin polypeptide sequences are provided. The full length human MATN3 AA sequence is provided above; the human MATN3 AA sequence contains the following active domains: 4 EGF repeats+VWFA domain. The full length human MATN1 AA sequence is also provided above; the human MATN1 AA sequence includes the following active domains: VWFA1+EGF repeat+VWFA2. The AA sequences of exemplary fragments of MATN1 and MATN3 are shown as underlined in the full-length sequence and shown again labeled as "active domain sequence". Full-length protein and active fragments are used in the methods described herein. Useful fragments (matrilin polypeptides) are greater than about 25 amino acids in length but less than the full-length protein, e.g., less than 486 amino acids. For example, a useful fragment is greater than 25 but less than 200, 250, 300, 350, 400, 450 or 480 amino acids in length. Examples of useful MATN3 and MATN1 polypeptides are shown above.

A Matrilin-3 polypeptide includes a polypeptide sequence having at least 80% 85%, 90%, 95%, 97%, 98%, or 99% sequence identity to SEQ ID NO: 1.

```
MATN3 mRNA comprises the following sequence.
                                                        (SEQ ID NO: 2)
   1 aaatccgagc ctcgcgtggg ctcctggccc ccgacggaca ccaccaggcc cacggagccc 61 accatgccgc gcccggcccc cgcgcgccgc ctcccgggac tcctcctgct gctctggccg 121 ctgctgctgc tgccctccgc cgcccccgac cccgtggccc gccgggctt ccggaggctg 181 gagacccgag gtcccggggg cagccctgga cgccgcccct ctcctgcggc tcccgacggc 241 gcgcccgctt ccgggaccag cgagcctggc cgcgcccgcg gtgcaggtgt ttgcaagagc 301 agaccettgg acctggtgtt tatcattgat agttctcgta gcgtacggcc cctggaattc 361 accaaagtga aaacttttgt ctcccggata atcgacactc tggacattgg gccagccgac 421 acgcgggtgg cagtggtgaa ctatgctagc actgtgaaga tcgagttcca actccaggcc 481 tacacagata agcagtccct gaagcaggcc gtgggtcgaa tcacaccctt gtcaacaggc 541 accatgtcag gcctagccca ccagacagca atggacgaag ccttcacagt ggaggcaggg 601 gctcgagagc cctcttctaa catccctaag gtggccatca ttgttacaga tgggaggccc 661 caggaccagg tgaatgaggt ggcggctcgg gcccaagcat ctggtattga gctctatgct 721 gtgggcgtgg accgggcaga catggcgtcc ctcaagatga tggccagtga gcccctagag 781 gagcatgttt tctacgtgga gacctatggg gtcattgaga aactttcctc tagattccag 841 gaaaccttct gtgcgctgga cccctgtgtg cttggaacac accagtgcca gcacgtctgc 901 atcagtgatg gggaaggcaa gcaccactgt gagtgtagcc aaggatacac cttgaatgcc 961 gacaagaaaa cgtgttcagc tcttgatagg tgtgctctta acacccacgg atgtgagcac 1021 atctgtgtga atgacagaag tggctcttat cattgtgagt gctatgaagg ttataccttg 1081 aatgaagaca ggaaaacttg ttcagctcaa gataaatgtg ctttgggtac ccatgggtgt 1141 cagcacacttt gtgtgaatga cagaacaggg tcccatcatt gtgaatgcta tgagggctac 1201 actctgaatg cagataaaaa aacatgttca gtccgtgaca agtgtgccct aggctctcat 1261 ggttgccagc acatttgtgt gagtgatggg gccgcatcct accactgtga ttgctatcct 1321 ggctacacct taaatgagga caagaaaaca tgttcagcca ctgaggaagc acgaagactt 1381 gtttccactg aagatgcttg tggatgtgaa gctacactgg cattccagga caaggtcagc 1441 tcgtatcttc aaagactgaa cactaaactt gatgacattt tggagaagtt gaaaataaat 1501 gaatatggac aaatacatcg ttaaattgct ccaattctc acctgaaaat gtggacagct 1561 tggtgtactt aatactcatg cattcttttg cacacctgtt attgccaatg ttcctgctaa
```

```
                                           -continued
1621 taatttgcca ttatctgtat taatgcttga atattactgg ataaattgta tgaagatctt 1681 ctgcagaatc agcatgattc ttccaaggaa atacatatgc agatacttat taagagcaaa 1741 ctttagtgtc tctaagttat gactgtgaaa tgattggtag gaaatagaat gaaaagttta 1801 gtgtttcttt atctactaat tgagccattt aattttaaa tgtttatatt agataaccat 1861 attcacaatg gaaactttag gtctagtttc ttttgatagt atttataata taaatcaatc 1921 ttattactga gagtgcaaat tgtacaaggt atttacacat acaacttcat ataactgaga 1981 tgaatgtaat tttgaactgt ttaacactttt ttgttttttg cttattttgt tggagtatta 2041 ttgaagatgt gatcaataga ttgtaataca catatctaaa aatagttaac acagatcaag 2101 tgaacattac attgccattt ttaattcatt ctggtctttg aaagaaatgt actactaaag 2161 agcactagtt gtgaatttag ggtgttaaac tttttaccaa gtacaaaaat cccaaattca 2221 ctttattatt ttgcttcagg atccaagtga caaagttata tatttataaa attgctataa 2281 atcgacaaaa tctaatgttg tcttttttaat gttagtgatc cacctgcctc agcctcccaa 2341 agtgctggga ttacaggctt gaaagtctaa cttttttttta cttatatatt tgatacatat 2401 aattcttttg gctttgaaac ttgcaacttt gagaacaaaa cagtccttta aattttgcac 2461 tgctcaattc tgttttttcgt ttgcattgtc tttaatataa taaaagttat tacctttaca 2521 tattatcatg tctattttg atgactcatc aattttgtct attaaagata tttctttaaa 2581 ttaaaaaaaa aaaaaaaaaa
```

A Matrilin-3 nucleic acid encodes a polypeptide that is at least 80% 85%, 90%, 95%, 97%, 98%, or 99% identical to SEQ ID NO: 1. A Matrilin-3 nucleic acid may be at least 60%, 65%, 70%, 75%, 80% 85%, 90%, 95%, 97%, 98%, or 99% identical to SEQ ID NO: 2 and encode a Matrilin-3 polypeptide.

Pharmaceutical Preparations

According to some embodiments, pharmaceutical preparations are provided comprising a therapeutically effective amount of a Matrilin-3 polypeptide or Matrilin-3 nucleic acid (a nucleic acid encoding a Matrilin-3 polypeptide). To form a Matrilin-3 composition for use in the invention, Matrilin-3 polypeptide or Matrilin-3 encoding expression viral vectors may be placed into a pharmaceutically acceptable suspension, solution or emulsion. Suitable mediums include saline and liposomal preparations.

A polypeptide of the present invention (derived from whatever source defined herein, including without limitation from synthetic, recombinant and non recombinant sources) may be used in a pharmaceutical composition when combined with a pharmaceutically acceptable carrier. Such compositions comprise a therapeutically effective amount of a Matrilin-3 polypeptide, and a pharmaceutically acceptable carrier. Such a composition may also be comprised of (in addition to peptide and a carrier) diluents, fillers, salts, buffers, stabilizers, solubilizers, and other materials well known in the art. The characteristics of the carrier will depend on the route of administration.

More specifically, pharmaceutically acceptable carriers may include sterile aqueous of non-aqueous solutions, suspensions, and emulsions. Examples of nonaqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils.

Intravenous vehicles include fluid and nutrient replenishers, electrolyte replenishers (such as those based on Ringer's dextrose), and the like.

Preservatives and other additives may also be present such as, for example, antimicrobials, antioxidants, chelating agents, and inert gases and the like. Further, a composition of Matrilin-3 transgenes may be lyophilized using means well known in the art, for subsequent reconstitution and use according to the invention.

A colloidal dispersion system may also be used for targeted gene delivery. Colloidal dispersion systems include macromolecule complexes, nanocapsules, microspheres, beads, and lipid-based systems including oil-in-water emulsions, micelles, mixed micelles, and liposomes. Liposomes are artificial membrane vesicles which are useful as delivery vehicles in vitro and in vivo. It has been shown that large unilamellar vesicles (LUV), which range in size from 0.2-4.0 μm can encapsulate a substantial percentage of an aqueous buffer containing large macro molecules. RNA, DNA and intact virions can be encapsulated within the aqueous interior and be delivered to cells in a biologically active form (Fraley, et al., Trends Biochem. Sci., 6: 77, 1981). In addition to mammalian cells, liposomes have been used for delivery of operatively encoding transgenes in plant, yeast and bacterial cells. In order for a liposome to be an efficient gene transfer vehicle, the following characteristics should be present: (1) encapsulation of the genes encoding the Matrilin-3 at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., Biotechniques, 6: 682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries.

Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted gene delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

Intra-Articular Injection

Intra-articular injection involves the injection of a medication directly into a joint space. Numerous drugs such as hyaluronic acid and corticosteroids are routinely administered in this manner. Matrilin is administered locally to a joint in the same manner to reduce inflammation, such as in osteoarthritis, bursitis, fibromyositis, or other causes, as well as to promote regeneration and repair of tissue, e.g., cartilage, within the joint. The method of administration is suitable for all articulating or synovial joints, e.g., knee, hip, elbow, shoulder, as well as other articulating structures such as vertebrae, ankles, wrists, fingers, or toes.

The needle or other delivery device is typically directed by anatomic landmarks, fluoroscopic guidance, and/or ultrasound guidance. The therapeutic matrilin composition is formulated and packaged for use using known methods and techniques. For example, it is supplied in milliliter quantity (e.g., 2 ml) vials (one injection per vial) or in prefilled syringes. A exemplary injection schedule is one injection per week for three to five weeks. Repeat courses are optionally performed after six months or as needed.

A knee joint can be injected several ways. One approach is to have the patient lie supine on the examination table with the knee flexed 90 degrees. In this position, the anterior portions of the medial and lateral joint lines are easily be palpated as dimples just medial or lateral to the inferior pole of the patella. Often, the medial joint line is easier to palpate and define and is chosen as the site of injection. Alternatively, the knee joint is approached with the knee extended, again with the patient lying supine. The superolateral edge of the patella is frequently the site of injection, but other quadrants of the knee near the patellar edges can also be chosen. With this approach (knee in extended position), the needle is generally aimed under the patella.

Whichever approach is used, the actual injection site can be marked with a fingernail imprint or the barrel of a pen. Next, sterile preparation with a disinfectant such as povidone iodine preparation (Betadine) and alcohol can be performed. A 22- to 25-gauge needle is typically used for the injection. Local anesthesia, e.g., lidocaine, is optionally administered before the injection. Alternatively, an ethyl chloride spray can be used for local anesthesia. Injection into other articular joints, e.g., hip, elbow, shoulder, is performed using known methods similar to that described above for the knee.

Tissue Engineering for Replacement or Repair of Osteochondral Tissue

At the present time, joint replacement is accomplished using metal, e.g., titanium prosthetic devices. Such devices, particularly areas of the devices such as the ends that will interface with endogenous tissue, e.g., bone or cartilage, following installation are dipped or coated with a matrilin-containing composition prior to joint replacement surgery. However, bioengineered artificial composite compositions represent an alternative to metal devices. In some cases, the entire device is biocomposite; in other cases, hybrid devices are part metal, part biocomposite. The biocomposite composition is fabricated to include matrilin. For example, an articular surface of a synovial joint can regenerate with a biological cue spatially embedded in an anatomically correct bioscaffold. For example, anatomically correct or compatible structures for hip replacements include those that correspond to an acetabulum and a femoral head. Similarly, structures for knee replacements or replair of tibial plateau include those that correspond to tibia and femoral head. For example, a prosthetic apparatus for total hip replacement may include a prosthetic femoral head comprising a partially spherical head portion configured to fit rotatably within a prosthetic acetabular cup seated in an acetabulum, the prosthetic femoral head also comprising a neck engagement portion configured to fixedly join a prosthetic femoral neck. Other structures such as prosthetic intervertebral discs are also within the invention.

An exemplary anatomically correct bioscaffold is constructed using a composite of poly-☐-caprolactone and hydroxyapatite (Lee et al., 2010, The Lancet 376: 440-448) and loaded/doped with biologically-active substances such as matrilin. The articular surface of unilateral proximal humeral condyles of the subject is surgically excised and replaced with bioscaffolds spatially infused with matrilin (as optionally other bioactive components). The articular surface of the synovial joint can regenerate without cell transplantation. Optionally, cells are also administered.

In another example, matrilin-containing materials are used to fill a defect in or on articular cartilage. The defect is large or small and is caused by disease or trauma such as a sport injury. For example, the sports injury is a meniscus break, tear, or degradation in a knee joint. Exemplary biocomposite materials include extra-cellular matrix (ECM)-based materials, e.g., type I/III collagen matrix (Chondro-Gide, Geistlich Biomaterials, Wolhusen, Switzerland), silk-based materials, porous tantalum (TM), or poly-epsilon-caprolactone scaffolds (PCL) (Mrosek et al., 2010, J. Orthop. Res. 28:141-8). A matrilin-containing biocomposite material biocomposite (acellular or cell-seeded) is used to fill articular cartilage or other orthochondral lesions in knees or other anatomical structures. Examplary biocomposite materials for defect repair are in the form of a paste or slurry and are administered by injection or infusion into the affected area for osteochondral defect repair.

Exemplary biocomposite materials for joint replacement and repair of osteochondral defects include U.S. Patent Publication 20110237701, 20110144752.

Pharmaceutical Pack or Kit

The present invention also provides a pharmaceutical pack or kit, comprising one or more containers filled with one or more of the ingredients of the pharmaceutical compositions and therapeutics of the present invention. Optionally associated with such container(s) may be a notice in the form prescribed by a governmental agency regulating the manufacture, use or sale of pharmaceuticals or biological products, which notice reflects approval by the agency of manufacture, use or sale for human administration.

Gene Therapy

In a specific embodiment of the present invention, nucleic acids comprising a sequence that encodes a Matrilin-3 polypeptide are administered to an individual by way of gene therapy. Gene therapy refers to therapy that is performed by the administration of a specific nucleic acid to a subject. In this embodiment of the present invention, the nucleic acid produces its encoded peptide(s), which then serve to exert a therapeutic effect by modulating function of an aforementioned disease or disorder. Any of the methodologies relating to gene therapy available within the art may be used in the practice of the present invention. (See e.g., Goldspiel, et al., Clin. Pharm. 12: 488 505 (1993)).

According to some embodiments, pharmaceutical preparations/compositions are provided that comprise a nucleic acid encoding a Matrilin-3 polypeptide that is part of an expression vector. In a specific embodiment, such a nucleic acid possesses a promoter that is operably linked to coding region(s) of a Matrilin-3 polypeptide. The promoter may be inducible or constitutive, and, optionally, tissue specific. In another specific embodiment, a nucleic acid molecule is used in which coding sequences (and any other desired sequences) are flanked by regions that promote homologous recombination at a desired site within the genome, thus providing for intra chromosomal expression of nucleic acids. (See e.g., Koller and Smithies, 1989. Proc Natl Acad Sci USA 86: 8932 8935).

Delivery of the therapeutic nucleic acid into a patient may be either direct (i.e., the patient is directly exposed to the nucleic acid or nucleic acid containing vector) or indirect (i.e., cells are first transformed with the nucleic acid in vitro, then transplanted into the patient). These two approaches are known, respectively, as in vivo or ex vivo gene therapy. In a specific embodiment of the present invention, a nucleic acid is directly administered in vivo, where it is expressed to produce the encoded product. This may be accomplished by any of numerous methods known in the art including, but not limited to, constructing said nucleic acid as part of an appropriate nucleic acid expression vector and administering the same in a manner such that it becomes intracellular (e.g., by infection using a defective or attenuated retroviral or other viral vector; see U.S. Pat. No. 4,980,286); directly injecting naked DNA; using microparticle bombardment (e.g., a "Gene Gun®; Biolistic, DuPont); coating said nucleic acids with lipids; using associated cell surface receptors/transfecting agents; encapsulating in liposomes, microparticles, or microcapsules; administering it in linkage to a peptide that is known to enter the nucleus; or by administering it in linkage to a ligand predisposed to receptor mediated endocytosis (see, e.g., Wu and Wu, 1987. J Biol Chem 262: 4429 4432), which can be used to "target" cell types that specifically express the receptors of interest, etc.

In another specific embodiment of the present invention, a nucleic acid ligand complex may be produced in which the ligand comprises a fusogenic viral peptide designed so as to disrupt endosomes, thus allowing the nucleic acid to avoid subsequent lysosomal degradation. In yet another specific embodiment, the nucleic acid may be targeted in vivo for cell specific endocytosis and expression, by targeting a specific receptor. (See e.g., PCT Publications WO 92/06180; WO93/14188 and WO 93/20221). Alternatively, the nucleic acid may be introduced intracellularly and incorporated within a host cell genome for expression by homologous recombination. (See e.g., Zijlstra, et al., 1989. Nature 342: 435 438).

In another specific embodiment, a viral vector that contains nucleic acids encoding a Matrilin-3 polypeptide is utilized. For example, retroviral vectors may be employed (see, e.g., Miller, et al., 1993. Meth Enzymol 217: 581 599) that have been modified to delete those retroviral specific sequences that are not required for packaging of the viral genome, with its subsequent integration into host cell DNA. Nucleic acids may be cloned into a vector that facilitates delivery of the genes into a patient. (See e.g., Boesen, et al., 1994. Biotherapy 6: 291 302; Kiem, et al., 1994. Blood 83: 1467 1473). Additionally, adenovirus may be used as an especially efficacious "vehicle" for the delivery of genes to the respiratory epithelia. Other targets for adenovirus based delivery systems are liver, central nervous system, endothelial cells, and muscle. Adenoviruses also possess advantageous abilities to infect non dividing cells. For a review see, e.g., Kozarsky and Wilson, 1993. Curr Opin Gen Develop 3: 499 503. Adenovirus associated virus (AAV) has also been proposed for use in gene therapy. (See e.g., Walsh, et al., 1993. Proc Soc Exp Biol Med 204: 289 300).

An additional approach to gene therapy in the practice of the present invention involves transferring a gene into cells in in vitro tissue culture by such methods as electroporation, lipofection, calcium phosphate mediated transfection, viral infection, or the like. Generally, the methodology of transfer includes the concomitant transfer of a selectable marker to the cells. The cells are then placed under selection pressure (e.g., antibiotic resistance) so as to facilitate the isolation of those cells that have taken up, and are expressing, the transferred gene. Those cells are then delivered to a patient. In a specific embodiment, prior to the in vivo administration of the resulting recombinant cell, the nucleic acid is introduced into a cell by any method known within the art including, but not limited to: transfection, electroporation, microinjection, infection with a viral or bacteriophage vector containing the nucleic acid sequences of interest, cell fusion, chromosome mediated gene transfer, microcell mediated gene transfer, spheroplast fusion, and similar methodologies that ensure that the necessary developmental and physiological functions of the recipient cells are not disrupted by the transfer. (See e.g., Loeffler and Behr, 1993. Meth Enzymol 217: 599 618). The chosen technique should provide for the stable transfer of the nucleic acid to the cell, such that the nucleic acid is expressible by the cell. Preferably, said transferred nucleic acid is heritable and expressible by the cell progeny.

In preferred embodiments of the present invention, the resulting recombinant cells may be delivered to a patient by various methods known within the art including, but not limited to, injection of cells (e.g., subcutaneously or directly into a joint) or application of cells as a graft into or onto joint tissue of the patient The total amount of cells that are envisioned for use depend upon the desired effect, patient state, and the like, and may be determined by one skilled within the art.

Cells into which a nucleic acid can be introduced for purposes of gene therapy encompass any desired, available cell type, and may be xenogeneic, heterogeneic, syngeneic, or autogeneic. Cell types include, but are not limited to, chondrocytes or chondrogenic cells, or osteocytes or osteogenic cells. In a preferred embodiment, the cells utilized for gene therapy are autologous to the patient.

Viral Vectors

Broadly, gene therapy seeks to transfer new genetic material to the cells of a patient with resulting therapeutic benefit to the patient. Such benefits include treatment or prophylaxis of a broad range of diseases, disorders and other conditions.

Ex vivo gene therapy approaches involve modification of isolated cells, which are then infused, grafted or otherwise transplanted into the patient. See, e.g., U.S. Pat. Nos. 4,868,116, 5,399,346 and 5,460,959, incorporated by reference herein in their entireties. In vivo gene therapy seeks to directly target host patient tissue in vivo.

Viruses useful as gene transfer vectors include papovavirus, adenovirus, vaccinia virus, adeno-associated virus, herpes virus, and retroviruses. Suitable retroviruses include the group consisting of HIV, SIV, FIV, EIAV, MoMLV.

Preferred viruses for treatment of disorders of the joint are lentiviruses and adeno-associated viruses. Both types of viruses can integrate into the genome without cell divisions, and both types have been tested in pre-clinical animal studies for indications in the joint, in particular in the joint.

Methods for preparation of AAV are described in the art, e.g. U.S. Pat. No. 5,677,158, U.S. Pat. No. 6,309,634, and U.S. Pat. No. 6,451,306, incorporated by reference herein in their entireties.

A special and preferred type of retroviruses include the lentiviruses which can transduce a cell and integrate into its genome without cell division. Thus preferably the vector is a replication-defective lentivirus particle. Such a lentivirus particle can be produced from a lentiviral vector comprising a 5' lentiviral LTR, a tRNA binding site, a packaging signal, a promoter operably linked to a polynucleotide signal encoding said fusion protein, an origin of second strand DNA synthesis and a 3' lentiviral LTR.

Retroviral vectors are the vectors most commonly used in human clinical trials, since they carry 7-8 kb and since they have the ability to infect cells and have their genetic material stably integrated into the host cell with high efficiency. See, e.g., WO 95/30761; WO 95/24929, incorporated by reference herein in their entireties. Oncovirinae require at least one round of target cell proliferation for transfer and integration of exogenous nucleic acid sequences into the patient. Retroviral vectors integrate randomly into the patient's genome.

Three classes of retroviral particles have been described; ecotropic, which can infect murine cells efficiently, and amphotropic, which can infect cells of many species. A third class include xenotropic retrovirus which can infect cells of another species than the species which produced the virus. Their ability to integrate only into the genome of dividing cells has made retroviruses attractive for marking cell lineages in developmental studies and for delivering therapeutic or suicide genes to cancers or tumors. These vectors may be particularly useful in the joint for cancer treatment, where there is a relative lack of cell division in adult patients.

For use in human patients, the retroviral vectors must be replication defective. This prevents further generation of infectious retroviral particles in the target tissue-instead the replication defective vector becomes a "captive" transgene stable incorporated into the target cell genome. Typically in replication defective vectors, the gag, env, and pol genes have been deleted (along with most of the rest of the viral genome). Heterologous DNA is inserted in place of the deleted viral genes. The heterologous genes may be under the control of the endogenous heterologous promoter, another heterologous promoter active in the target cell, or the retroviral 5' LTR (the viral LTR is active in diverse tissues). Typically, retroviral vectors have a transgene capacity of about 7-8 kb.

Expression Vectors

Construction of vectors for recombinant expression of Matrilin-3 for use in the invention may be accomplished using conventional techniques which do not require detailed explanation to one of ordinary skill in the art. For review, however, those of ordinary skill may wish to consult Maniatis et al., in Molecular Cloning: A Laboratory Manual, Cold Spring Harbor Laboratory, (NY 1982). Briefly, construction of recombinant expression vectors employs standard ligation techniques. For analysis to confirm correct sequences in vectors constructed, the genes are sequences using, for example, the method of Messing, et al., (Nucleic Acids Res., 9: 309-, 1981), the method of Maxam, et al., (Methods in Enzymology, 65: 499, 1980), or other suitable methods which will be known to those skilled in the art.

Size separation of cleaved fragments is performed using conventional gel electrophoresis as described, for example, by Maniatis, et al., (Molecular Cloning, pp. 133-134, 1982). Expression of a gene is controlled at the transcription, translation or post-translation levels. Transcription initiation is an early and critical event in gene expression. This depends on the promoter and enhancer sequences and is influenced by specific cellular factors that interact with these sequences. The transcriptional unit of many genes consists of the promoter and in some cases enhancer or regulator elements (Banerji et al., Cell 27: 299 (1981); Corden et al., Science 209: 1406 (1980); and Breathnach and Chambon, Ann Rev. Biochem. 50: 349 (1981)). For retroviruses, control elements involved in the replication of the retroviral genome reside in the long terminal repeat (LTR) (Weiss et al., eds., The molecular biology of tumor viruses: RNA tumor viruses, Cold Spring Harbor Laboratory, (NY 1982)). Moloney murine leukemia virus (MLV) and Rous sarcoma virus (RSV) LTRs contain promoter and enhancer sequences (Jolly et al., Nucleic Acids Res. 11: 1855 (1983); Capecchi et al., In: Enhancer and eukaryotic gene expression, Gulzman and Shenk, eds., pp. 101-102, Cold Spring Harbor Laboratories (NY 1991). Other potent promoters include those derived from cytomegalovirus (CMV) and other wild-type viral promoters.

Promoter and enhancer regions of a number of non-viral promoters have also been described (Schmidt et al., Nature 314: 285 (1985); Rossi and decrombrugghe, Proc. Natl. Acad. Sci. USA 84: 5590-5594 (1987)). Methods for maintaining and increasing expression of transgenes in quiescent cells include the use of promoters including collagen type I (1 and 2) (Prockop and Kivirikko, N. Eng. J. Med. 311: 376 (1984); Smith and Niles, Biochem. 19: 1820 (1980); de Wet et al., J. Biol. Chem., 258: 14385 (1983)), SV40 and LTR promoters.

According to one embodiment of the invention, the promoter is a constitutive promoter selected from the group consisting of: ubiquitin promoter, CMV promoter, JeT promoter (U.S. Pat. No. 6,555,674), SV40 promoter, and Elongation Factor 1 alpha promoter (EF1-alpha).

Examples of Inducible/Repressible Promoters Include: Tet-on, Tet-Off, Rapamycin-Inducible Promoter, Mx1.

In addition to using viral and non-viral promoters to drive transgene expression, an enhancer sequence may be used to increase the level of transgene expression. Enhancers can increase the transcriptional activity not only of their native gene but also of some foreign genes (Armelor, Proc. Natl. Acad. Sci. USA 70: 2702 (1973)). For example, in the present invention collagen enhancer sequences may be used with the collagen promoter 2 (I) to increase transgene expression. In addition, the enhancer element found in SV40 viruses may be used to increase transgene expression. This enhancer sequence consists of a 72 base pair repeat as described by Gruss et al., Proc. Natl. Acad. Sci. USA 78: 943 (1981); Benoist and Chambon, Nature 290: 304 (1981), and Fromm and Berg, J. Mol. Appl. Genetics, 1: 457 (1982), all of which are incorporated by reference herein. This repeat sequence can increase the transcription of many different viral and cellular genes when it is present in series with various promoters (Moreau et al., Nucleic Acids Res. 9: 6047 (1981).

Further expression enhancing sequences include but are not limited to Woodchuck hepatitis virus post-transcriptional regulation element, WPRE, SP163, rat Insulin-intron or other introns, CMV enhancer, and Chicken [beta]-globin insulator or other insulators.

Transgene expression may also be increased for long term stable expression using cytokines to modulate promoter activity. Several cytokines have been reported to modulate the expression of transgene from collagen 2 (I) and LTR promoters (Chua et al., connective Tissue Res., 25: 161-170 (1990); Elias et al., Annals N.Y. Acad. Sci., 580: 233-244 (1990)); Seliger et al., J. Immunol. 141: 2138-2144 (1988) and Seliger et al., J. Virology 62: 619-621 (1988)). For example, transforming growth factor (TGF), interleukin (IL)-I, and interferon (INF) down regulate the expression of transgenes driven by various promoters such as LTR. Tumor necrosis factor (TNF) and TGF 1 up regulate, and may be used to control, expression of transgenes driven by a promoter. Other cytokines that may prove useful include basic fibroblast growth factor (bFGF) and epidermal growth factor (EGF).

Collagen promoter with the collagen enhancer sequence (Coll (E)) may also be used to increase transgene expression by suppressing further any immune response to the vector which may be generated in a treated brain notwithstanding its immune-protected status. In addition, anti-inflammatory agents including steroids, for example dexamethasone, may be administered to the treated host immediately after vector composition delivery and continued, preferably, until any cytokine-mediated inflammatory response subsides. An immunosuppression agent such as cyclosporin may also be administered to reduce the production of interferons, which downregulates LTR promoter and Coll (E) promoter-enhancer, and reduces transgene expression.

The vector may comprise further sequences such as a sequence coding for the Cre-recombinase protein, and LoxP sequences. A further way of ensuring temporary expression of the neublastin is through the use of the Cre-LoxP system which results in the excision of part of the inserted DNA sequence either upon administration of Cre-recombinase to the cells (Daewoong et al, Nature Biotechnology 19:929-933) or by incorporating a gene coding for the recombinase into the virus construct (Pluck, Int J Exp Path, 77:269-278). Incorporating a gene for the recombinase in the virus construct together with the LoxP sites and a structural gene (a neublastin in the present case) often results in expression of the structural gene for a period of approximately five days.

Medical Use and Methods of Treatment

In one aspect the invention relates to the use of the vector according to the invention for the preparation of a medicament for the treatment of a joint disorder. In some embodiments, the joint disorder is osteoarthritis. Treatment is not only intended to be curative treatment but also preventive (not absolute prevention) or prophylactic treatment. Treatment may also be ameliorative or symptomatic.

The pharmaceutical preparations of the present invention may be delivered to a subject in need thereof using any suitable method. In some embodiments, the pharmaceutical preparations of the present invention are delivered to the joint of an individual in need thereof.

Cultured Cells

Cells may be cultured ex vivo in the presence of peptides of the present invention in order to proliferate or to produce a desired effect on or activity in such cells. Treated cells can then be introduced in vivo for therapeutic purposes.

Methods of Administration

Suitable methods of administration include, but are not limited to, intradermal, intramuscular, intraperitoneal, intravenous, subcutaneous, intranasal, epidural, and oral routes. The therapeutic compositions of the present invention may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

Various delivery systems are known and can be used to administer a pharmaceutical preparation of the present invention including, but not limited to: (i) encapsulation in liposomes, microparticles, microcapsules; (ii) recombinant cells capable of expressing Matrilin-3; (iii) receptor mediated endocytosis (see, e.g., Wu and Wu, 1987. J Biol Chem 262:4429 4432); (iv) construction of a Matrilin-3 nucleic acid as part of a retroviral or other vector, and the like.

In one embodiment of the present invention, the Matrilin-3 preparation may be delivered in a vesicle, in particular a liposome. In a liposome, the peptide of the present invention is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,837,028; and U.S. Pat. No. 4,737,323, all of which are incorporated herein by reference.

In yet another embodiment, the Matrilin-3 preparation can be delivered in a controlled release system including, but not limited to: a delivery pump (see, e.g., Saudek, et al., 1989. New Engl J Med 321:574 and a semi permeable polymeric material (see, e.g., Howard, et al., 1989. J Neurosurg 71:105). Additionally, the controlled release system can be placed in proximity of the therapeutic target thus requiring only a fraction of the systemic dose. See, e.g., Goodson, In: Medical Applications of Controlled Release 1984. (CRC Press, Bocca Raton, Fla.).

In a specific embodiment of the present invention, where the Matrilin-3 preparation comprises a nucleic acid encoding a peptide, the nucleic acid may be administered in vivo to promote expression of its encoded peptide, by constructing it as part of an appropriate nucleic acid expression vector and administering it so that it becomes intracellular (e.g., by use of a retroviral vector, by direct injection, by use of microparticle bombardment, by coating with lipids or cell surface receptors or transfecting agents, or by administering it in linkage to a homeobox like peptide which is known to enter the nucleus (see, e.g., Joliot, et al., 1991. Proc Natl Acad Sci USA 88:1864 1868), and the like. Alternatively, a nucleic acid Matrilin-3 preparation can be introduced intracellularly and incorporated within host cell DNA for expression, by homologous recombination.

EXAMPLES

It is understood that modifications which do not substantially affect the activity of the various embodiments of this invention are also provided within the definition of the invention provided herein. Accordingly, the disclosed examples are intended to illustrate but not limit the present invention. While the claimed invention has been described in detail and with reference to specific embodiments thereof, it will be apparent to one of ordinary skill in the art that various changes and modifications can be made to the claimed invention without departing from the spirit and scope thereof. Thus, for example, those skilled in the art will recognize, or be able to ascertain, using no more than routine experimentation, numerous equivalents to the specific substances and procedures described herein. Such equivalents are considered to be within the scope of this invention, and are covered by the following claims.

Example 1. Matrilin-3 is Required for Maintaining Type II Collagen and Aggrecan Synthesis and Inhibiting Expression of Osteoarthritis Associated Matrix Proteases Induced by IL-1β

Development of osteoarthritis is due to an imbalance between synthesis and degradation of extracellular matrix network, which is responsible for structural and mechanical properties of articular cartilage. In this study, we show that MATN3, in addition to its structural role of connecting type II collagen fibrils and aggrecan, also plays a regulatory role in maintaining the expression levels of these two major components of ECM in cartilage. This is demonstrated both in vivo and in vitro. Furthermore, MATN3 reverses the stimulatory effect of IL-1β on matrix proteases including Matrix Metalloproteinase 13 (MMP-13) and ADAMTS-5. They are the major collagenase and aggrecanase that are responsible for degradation of cartilage ECM network during OA. The results show that the accelerated OA pathogenesis in MATN3 KO mice may be attributed not only to its own structural role in the matrix, but also to its previously undiscovered function of regulating other major cartilage ECM molecules and the matrix proteases that degrade them. The finding that MATN3 reverses the effects of IL-1β on expression of Col II, MMP-13, and ADAMTS-5 in chondrocytes shows MATN3 as a chondroprotective agent for treatment of OA.

The data provided here provides evidence that Matrilin-3 has a role in regulating the expression of other major ECM components in articular cartilage as well as OA associated matrix proteases in response to IL1-β.

Methods mRNA Isolation. Total mRNA was isolated from the hind limbs of newborn MATN3 KO mice and newborn WT mice of the same genetic background (C57BL/6J) using the RNAqueous kit (AMBION). There were 5 mice in each group (n=5). Cell Culture. Cell culture experiments were conducted using the C28/12 immortalized human chondrocyte cell line. Cells were always seeded at 400,000 cells/well 24-hours prior to treatment in 6-well culture plates using DMEM/F12 (1:1) cell culture media (GIBCO) containing 10% FBS. Cells were serum starved for 5 hours prior to exposure to experimental treatment conditions. After treatment, mRNA was isolated from cell lysates using the RNAqueous kit and reverse transcribed into cDNA using the iScript cDNA Synthesis kit (BIO-RAD). All experiments were done in biological triplicates.

RT-PCR. Real-time PCR was conducted on the cDNA of mouse whole limbs using primers specific to mouse collagen II and aggrecan. Likewise, primers specific for human MMP-13, collagen II, and ADAMTS5 were used to analyze gene expression in C28/12 cells.

Results

Figure 1:
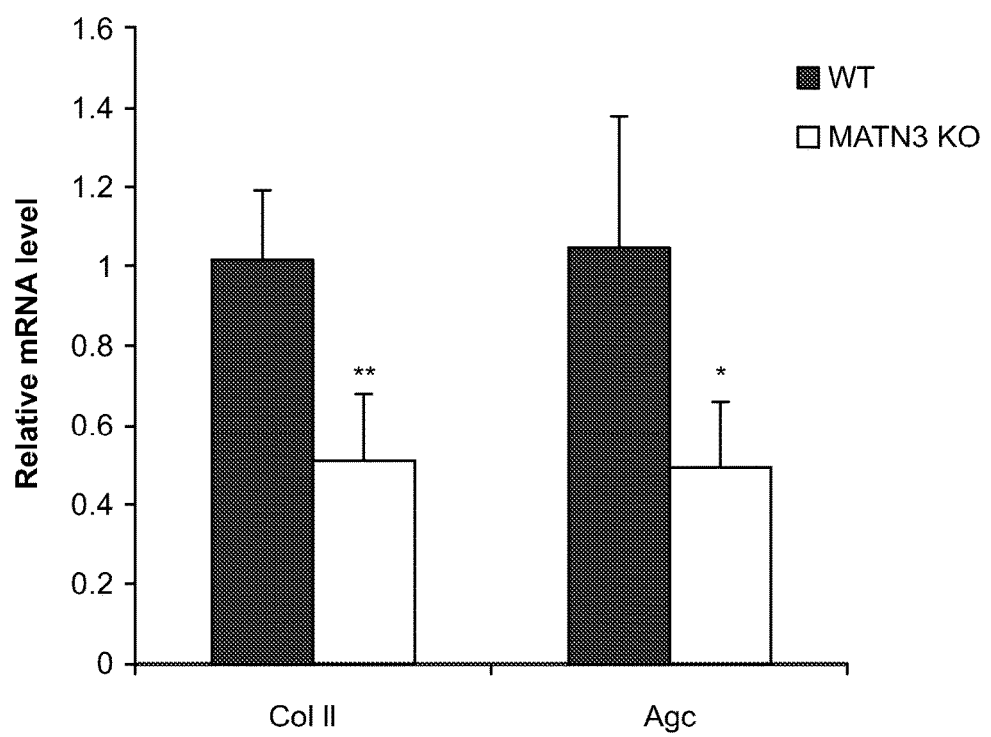
FIG. 1 is a bar graph showing that MATN3 KO mice expressed significantly lower levels of collagen II and aggrecan compared to WT mice of the same genetic background. Single-asterisk ($p<0.05$) and double-asterisk ($p<0.01$) indicate statistically significant differences between mRNA levels between WT and MATN3 KO mice. There were 5 mice in each group (n=5).

To determine whether the lack of MATN3 affects the expression of other ECM genes in vivo, we quantified the mRNA levels of collagen II and aggrecan in the hind limbs of new born mice. MATN3 KO mice expressed significantly lower levels of collagen II and aggrecan compared to WT mice of the same genetic background (FIG. 1).

Figure 2:
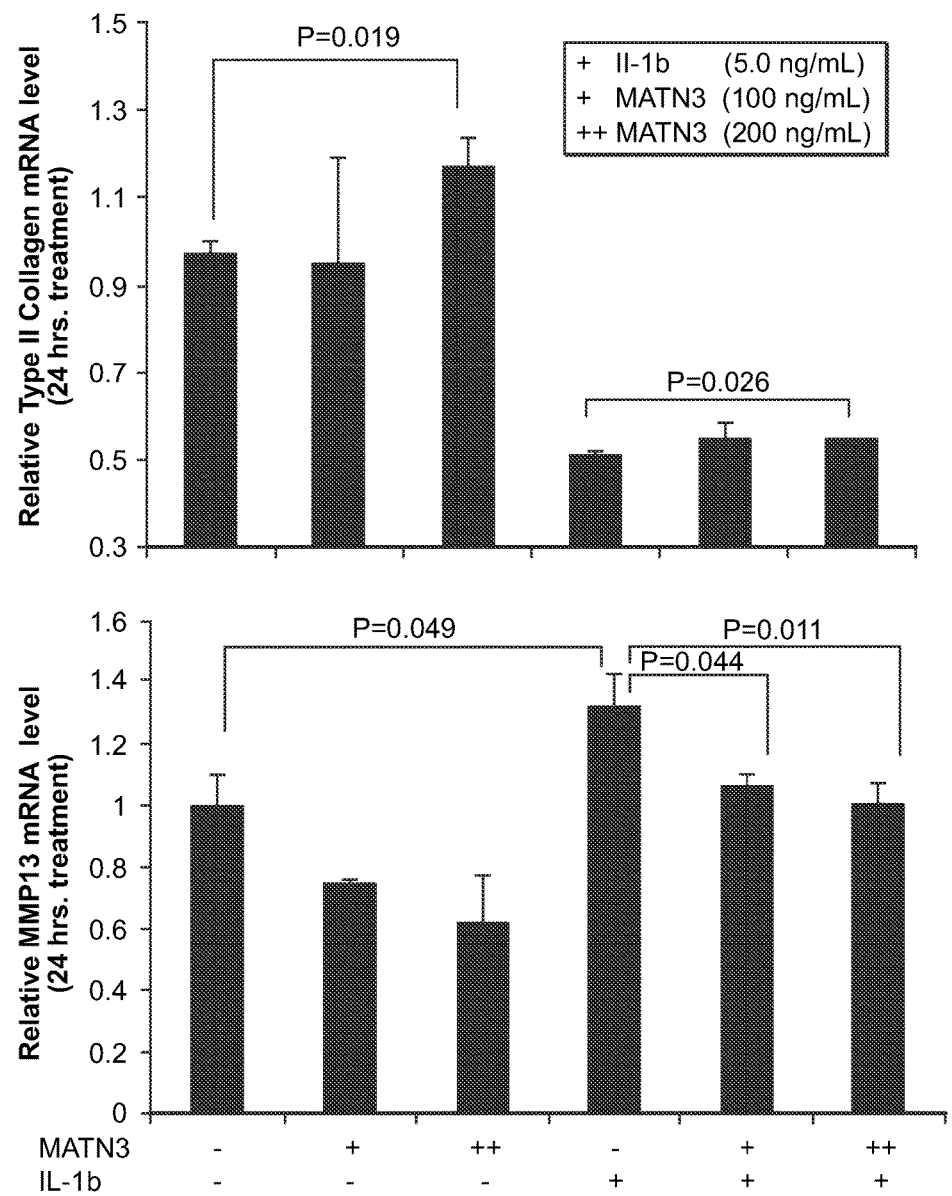
FIG. 2 is a series of bar graphs showing that MATN3 upregulated collagen II and downregulated MMP-13 expression in a dose-dependent manner. The presence of IL-1β suppressed the expression of Col II while stimulating the expression of MMP-13. MATN3 reversed the stimulation of MMP13 mRNA level by IL-1β, but only partially rescued the inhibitory effect of IL-1β on Col II.

To determine whether MATN3 affects expression of cartilage and OA related genes in vitro, we incubated C28/12 human chondrocytes with recombinant human MATN3 protein in the presence or absence of IL-1β. In the absence of IL-1β, MATN3 upregulated collagen II and downregulated MMP-13 expression in a dose-dependent manner (FIG. 2). The presence of IL-1b suppressed the expression of Col II while stimulating the expression of MMP-13. MATN3 reversed the stimulation of MMP13 mRNA level by IL-1β, but only partially rescued the inhibitory effect of IL-1β on Col II (FIG. 2).

Figure 3:
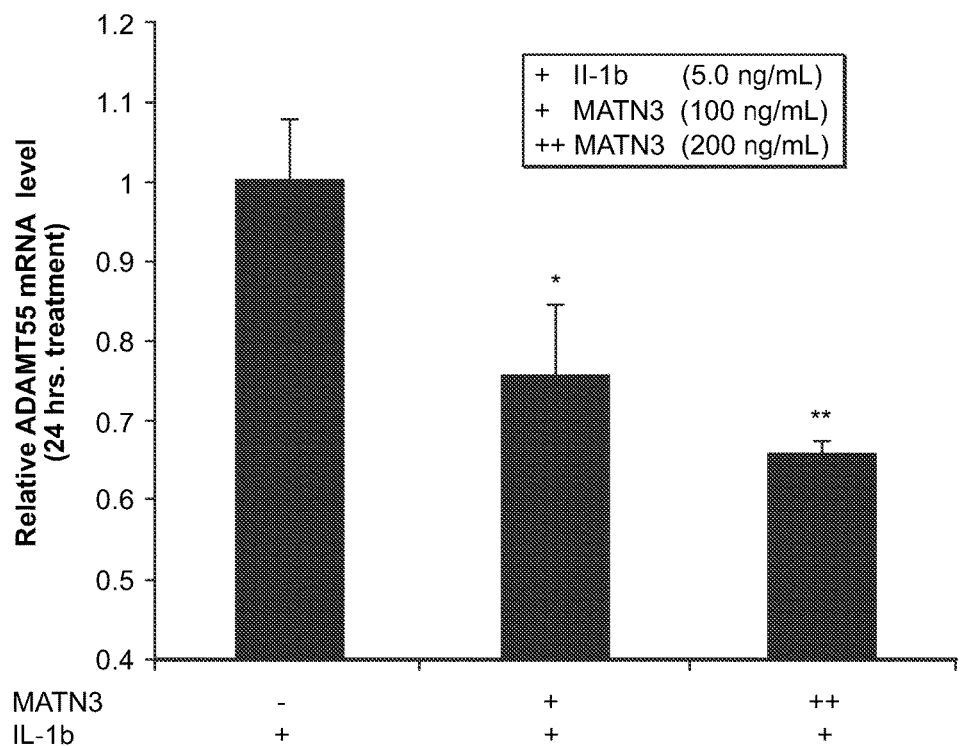
FIG. 3 is a bar graph showing that recombinant MATN3 inhibited the IL-1β stimulated expression of ADAMTS-5 in a dose-dependent manner.

In addition, recombinant MATN3 also inhibited the IL-1β stimulated expression of ADAMTS-5 in a dose-dependent manner (FIG. 3).

Example 2. Matrilin-3 Inhibits MMP-13 Expression

Figure 4:
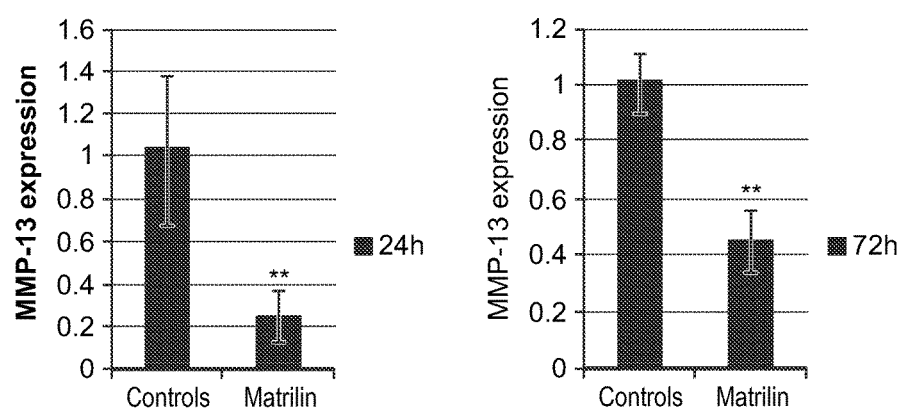
FIG. 4 is a bar graph showing that treating human chondrocytes with recombinant human MATN3 protein inhibits joint degrading protease MMP-13 expression at 24 and 72 hours post treatment. Recombinant human MATN3 protein was used at a concentration of 200 ng/ml for this experiment. Double asterisks ** indicate statistically significant differences of $p \leq 0.01$ between groups. Data are representative of 3 individual experiments.

As was discussed above, treating chondrocytes with recombinant human matrilin-3 protein inhibits MMP-13 expression at 24 hours post cell culture treatment. FIG. 4 shows that matrilin-3's inhibition of MMP-13 lasts well into the 72 hour mark post treatment.

Figure 5:
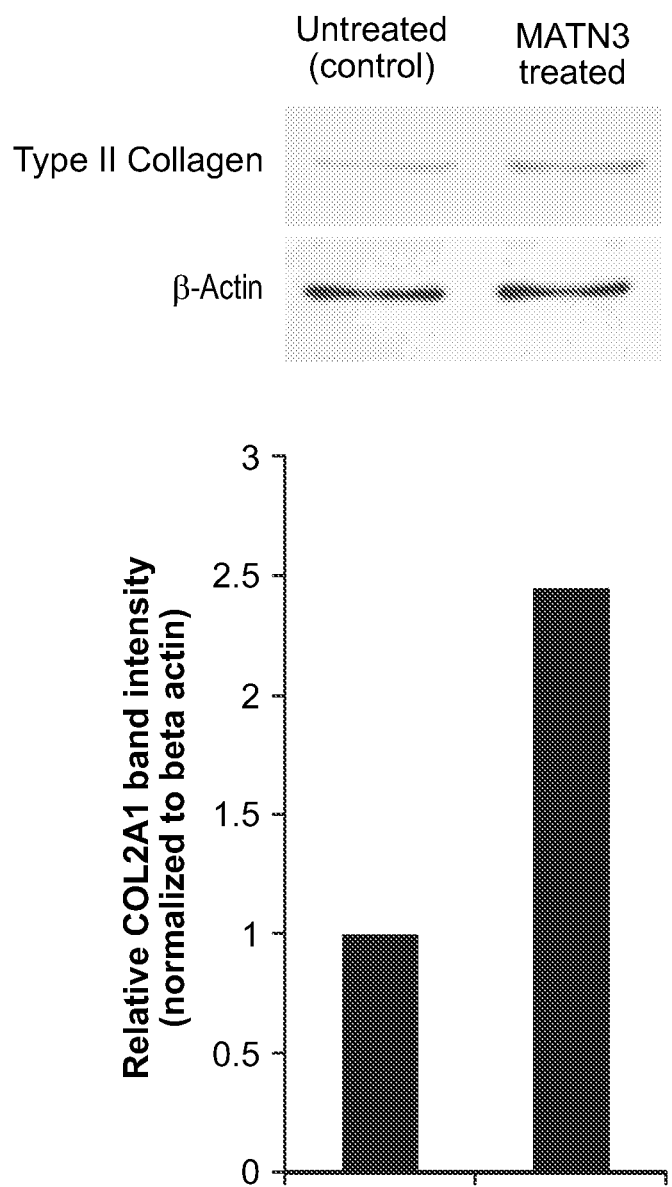
FIG. 5 is a photograph of the results of a Western blot assay and a bar graph showing normalized band intensities for semi quantitative analysis. Primary human chondrocytes treated with 200 ng/ml of recombinant human MATN3 protein for 48 hours exhibit enhanced collagen 2 protein levels as shown here by western blot analysis.

Example 3. Matrilin-3 Enhances Collagen 2 Protein Levels in Chondrocyte Cultures In addition to stimulating collagen 2 gene expression, MATN3 also enhanced collagen 2 protein levels in monolayer primary chondrocyte cell culture (FIG. 5).

Example 4. Matrilin-3 Stimulates Chondrogenic Gene Expression and has Potent Anti-Inflammatory Properties Recombinant human MATN3 protein was found to enhance the gene expression of major structural components of cartilage (e.g., collagen 2, aggrecan) as well as inhibit the gene expression of catabolic proteases linked to joint disease (i.e. MMP-13, ADAMTS-4, ADAMTS-5). MATN3 stimulated the production of the anti-inflammatory protein known as interleukin-1 receptor antagonist (IL-1Ra).

Figure 6B:
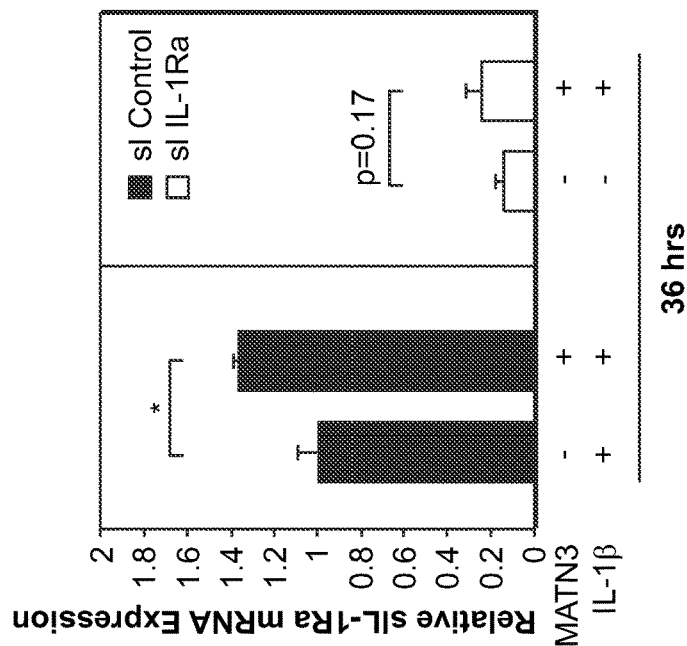
FIGS. 6A-C are a series of bar graphs showing gene expression analysis. Knocking down all isoforms of IL-1Ra via IL1RN siRNA treatment reduces the IL-1β induction of this gene as observed at two time points (24, 36 hours) post cell culture treatment (A, B). This also consequently results in the significant reduction of soluble IL-Ra protein levels in PHC cell supernatants after 24 hours (C). PHCs treated with a nonspecific scrambled siRNA construct is used as the control group. For these experiments, human recombinant MATN3 protein is used at 200 ng/ml. Recombinant human IL-1β protein treatment was 5.0 ng/ml. Asterisks indicate statistically significant differences of $p<0.05$ between groups. Data are representative of 3 individual experiments.
Figure 6A:
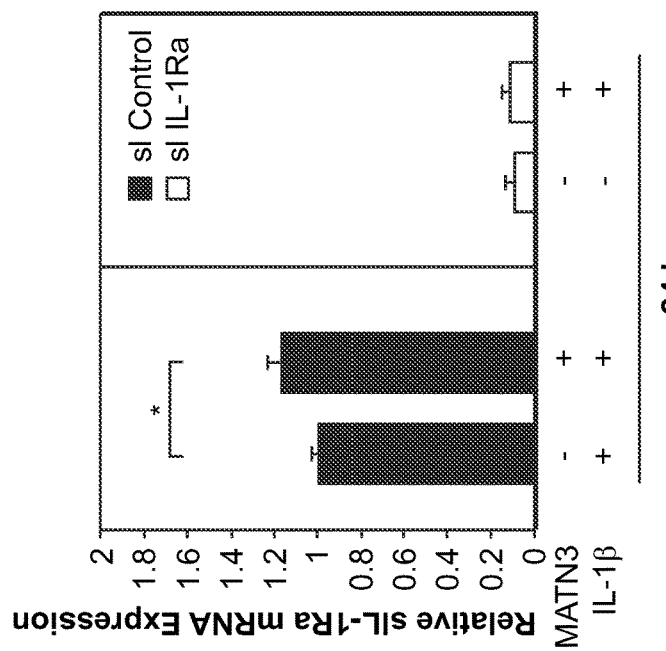
Figure 7A:
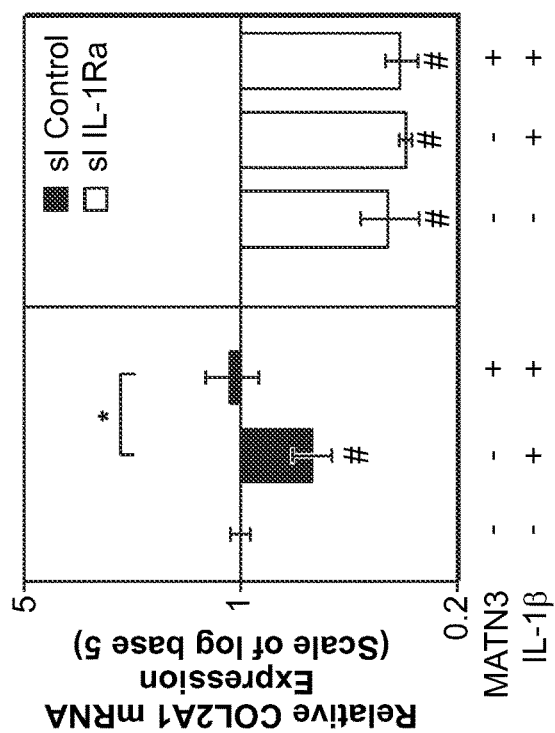
FIGS. 7A-D are a series of bar graphs showing gene expression analysis. Knocking down the IL-1R abolishes the ability of recombinant human MATN3 protein to maintain type II collagen (COL2A1) (A) and aggrecan (ACAN) gene expression (B) in PHCs that are challenged with IL-1β. A significant reduction in the basal gene expression of these markers is also evident in IL-1Ra-silenced PHCs. However, knocking down IL-1Ra only partially affects MATN3-induced inhibition of MMP-13 (C) and ADAMTS-5 (D) gene expression. The concentration of recombinant human MATN3 protein used was 200 ng/ml and IL-1β was 5.0 ng/ml. Gene expression analysis was conducted 36 hours post exposure to cell culture treatment conditions. Has marks (#) indicate statistical significance of $p \leq 0.05$ from the untreated group. Asterisks indicate statistically significant differences of $p \leq 0.05$ between groups. Data are representative of 3 individual experiments.
Figure 6C:
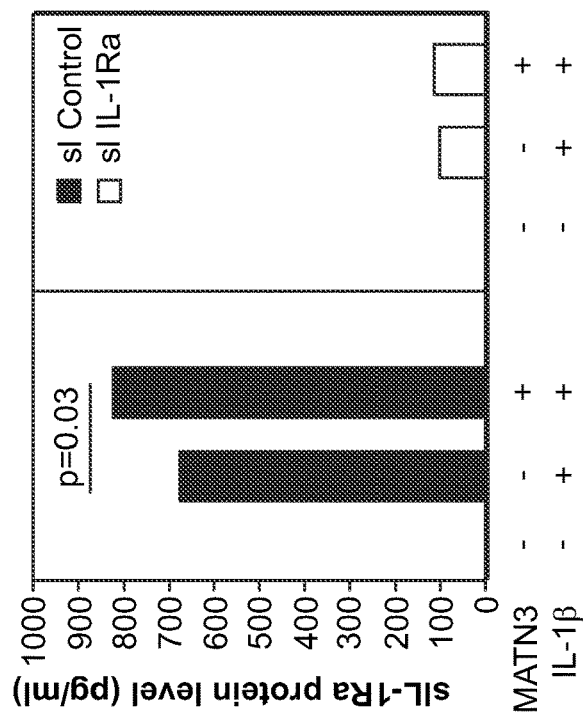
Figure 7B:
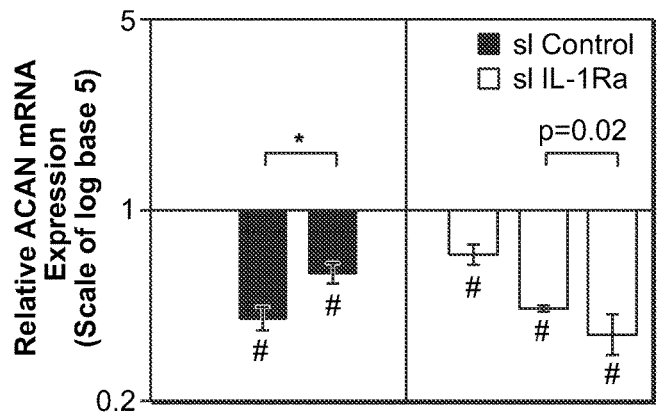
Figure 7C:
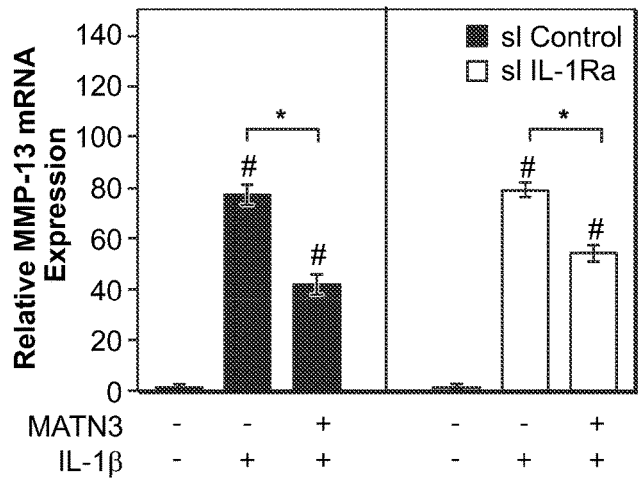
Figure 7D:
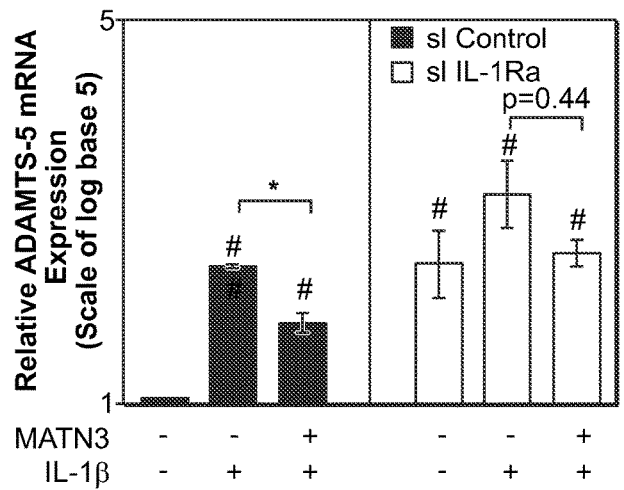

The data describe below are further evidence linking MATN3's chondroprotective effects to its ability to stimulate IL-1Ra production. In order to test whether MATN3 induced expression of collagen 2 and aggrecan are dependent on IL-1Ra, a small interfering RNA (siRNA) was used to silence all IL-1Ra isoforms in primary human chondrocytes (PHCs). The siRNA attenuated MATN3 induced IL-1Ra mRNA (FIG. 6A, 3B) and protein production (FIG. 6C). Treating cells with the siRNA that targets IL-1Ra abolishes the ability of recombinant human MATN3 protein to maintain collagen 2 (FIG. 7A) and aggrecan gene expression (FIG. 7B) in PHCs. Silencing IL-1Ra did not affect MATN3 induced inhibition of MMP13 (FIG. 7C). However, the absence of IL-1Ra does reduce MATN3's ability to inhibit ADAMTS-5 (FIG. 7D).

Figure 8C:
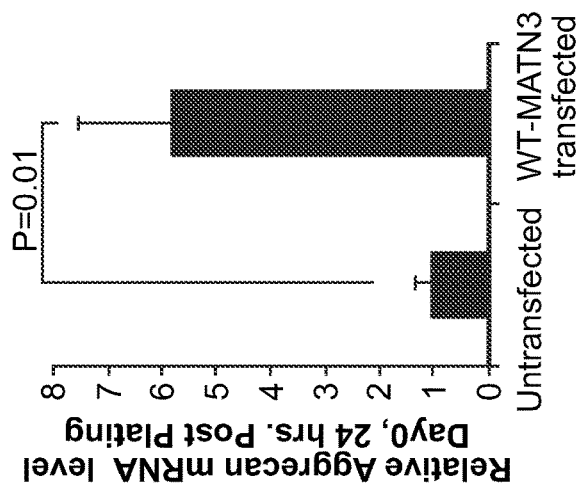
FIGS. 8A-C are a series of bar graphs showing gene expression analysis. ATDC5 cells stably transfected with the full length wild-type (WT) MATN3 gene exhibited enhanced IL-1Ra expression (A) as well as enhanced type II collagen (B) and aggrecan (C) expression. Triple asterisks *** indicate statistically significant differences of $p \leq 0.001$. Data are representative of 3 individual experiments.
Figure 8B:
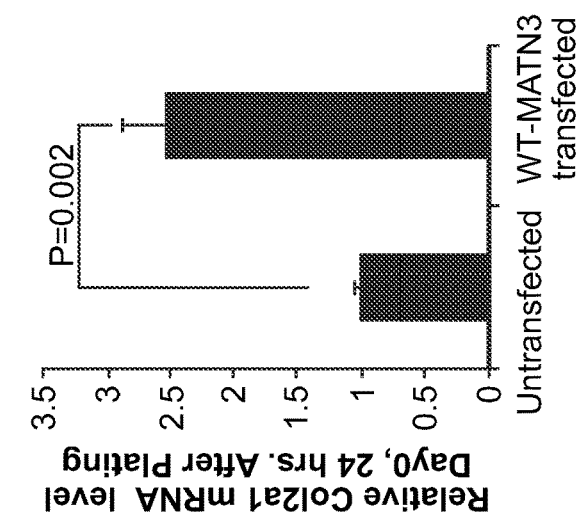
Figure 8A:
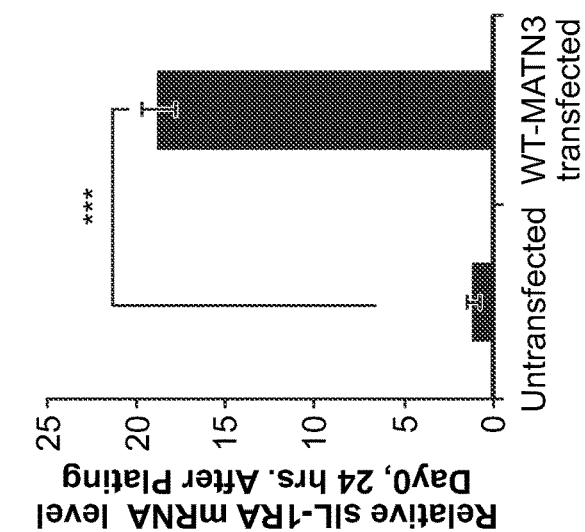

To reinforce the findings that MATN3 stimulates IL-1Ra, collagen 2 and aggrecan in cells, teratoma cell line ATDC5 was transfected with a pcDNA construct containing the full length MATN3 gene. MATN3 transfected cells exhibited enhanced IL-1Ra expression (FIG. 8A), and enhanced collagen 2 (FIG. 8B) and aggrecan expression (FIG. 8C), thereby confirming previous findings that exposure to MATN3 enhanced the expression of these 3 genes in chondrocytes.

Example 5. Matrilin-3 Enhances Cell and Whole Tissue Adhesion

Figure 9A:
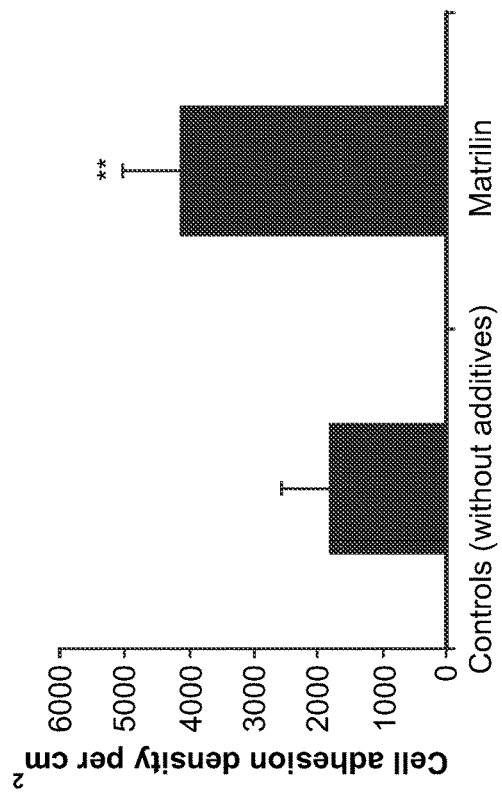
FIGS. 9A-B are bar graphs representing cell adhesion densities. ATDC5 cell adhesion density (A) and primary human chondrocyte adhesion density (B) increases when cells are plated on a cell culture dish that has MATN3 protein immobilized on the surface. Double asterisks ** indicate statistically significant differences of p<0.01. Data are representative of 9 individual experiments.
Figure 9B:
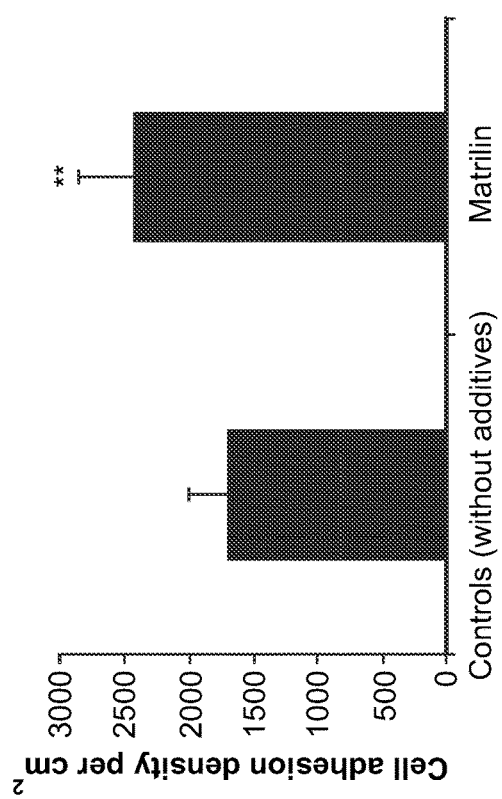

MATN3 is not only a bioactive molecule of anti-inflammation and a regulator of cartilage homeostasis, but it also enhances chondrocyte cell adhesion (FIGS. 9A-B, FIG. 10). Since MATN3 was shown to increase cell adhesion and protect joint degeneration, the ability of MATN3 to enhance cartilage whole tissue adhesion, integration and defect healing was tested, as illustrated in the explant tissue culture experiment diagram (FIG. 11A). In a cartilage transplantation model (van de Breevaart Bravenboer J., In de Maur C D, Bos P K, Feenstra L, Verhaar J A, Weinans H, van Osch G J Improved cartilage integration and interfacial strength after enzymatic treatment in a cartilage transplantation model. Arthritis Res Ther. 2004; 6(5):R469-76. Epub 2004 Aug. 6), a dermal biopsy punch was used to remove a 10 mm diameter sample from porcine knee cartilage, from which a 4 mm core was removed. Recombinant human MATN3 protein was then applied onto/into the core and the interior of the freshly punched defect (for the MATN3 Group). Agarose was also used as an inert material to cover the defect and stabilize the reagent (Coleman R M, Phillips J E, Lin A. Schwartz Z, Boyan B D, Guldberg R E. Characterization of a small animal growth plate injury model using microcomputed tomography. Bone 2010 June; 46(6):1555-63. Epub 2010 Feb. 20). For the Control Group, only agarose was applied. Cores were then replaced into the respective holes/defects and, after letting set for 72 hours, the ElectroForce was used to dislodge the core from the hole/defect and measured the exact force that was required to dislodge the core. Significantly more force was required to dislodge the core for the MATN3 group (FIG. 11B).

Both matrilin-1 and -3 behave similarly in enhancing cartilage formation and repair (FIG. 12). Thus, the compositions and methods described herein utilize members of the matrilin family (MATN1-4), their recombinant proteins and derived peptides or fragments thereof.

Example 6. Intraarticular Injection of Recombinant Matrilin-3 Reduces the Expression of Catabolic Matrix Proteases in Articular Cartilage During Osteoarthritis Using an art-recognized animal model, intraarticular injection of recombinant matrilin-3 into a rabbit knee reduced the mRNA levels of catabolic matrix proteinases in articular cartilage during OA. OA was induced in the knee joint of young adult rabbit by transaction of ACL and PCL and removal of medial meniscus for 2 weeks before weekly injection of recombinant matrilin-3 (2 ml of 200 ng/ml) for 6 weeks. At Day 56, articular cartilage was harvested from experimental (matrilin treated) or control (saline treated) knees. mRNA was isolated and quantified by quantitative PCR with 18SRNA as internal control (FIG. 13). These results indicate that local administration of matrilin in vivo leads to reduced inflammation and reduction in the severity and symptoms of osteoarthritis.

Definitions

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only not intended to be limiting. Other features and advantages of the invention will be apparent from the following detailed description and claims.

Purified compounds, e.g., proteins, peptides, or nucleic acids, are at least 60% by weight (dry weight) the compound of interest. Preferably, the preparation is at least 75%, more preferably at least 90%, and most preferably at least 99% or 100%, by weight the compound of interest. Purity is measured by any appropriate standard method, for example, by column chromatography, polyacrylamide gel electrophoresis, or HPLC analysis.

For the purposes of promoting an understanding of the embodiments described herein, reference will be made to preferred embodiments and specific language will be used to describe the same. The terminology used herein is for the purpose of describing particular embodiments only, and is not intended to limit the scope of the present invention. As used throughout this disclosure, the singular forms "a," "an," and "the" include plural reference unless the context clearly dictates otherwise. Thus, for example, a reference to "a composition" includes a plurality of such compositions, as well as a single composition, and a reference to "a therapeutic agent" is a reference to one or more therapeutic and/or pharmaceutical agents and equivalents thereof known to those skilled in the art, and so forth.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Reference to numeric ranges throughout this specification encompasses all numbers falling within the disclosed ranges. Thus, for example, the recitation of the range of about 1% to about 5% includes 1%, 2%, 3%, 4%, and 5%, as well as, for example, 2.3%, 3.9%, 4.5%, etc.

What is claimed is:

1. A method for promoting cartilage formation in a subject in need thereof, comprising administering to said subject a composition comprising a purified matrilin protein, thereby promoting cartilage formation in said subject, wherein said composition is administered directly into or onto the cartilage of an articulating joint or osteochondral tissue, and wherein said matrilin protein comprises the amino acid sequence of SEQ ID NO: 1, amino acids 29-440 of SEQ ID NO: 1, or SEQ ID NO: 4.

2. The method of claim 1, wherein said composition further comprises a matrilin-1 protein.

3. The method of claim 1, wherein said articulating joint comprises a knee, hip, elbow, or shoulder.

4. The method of claim 1, wherein said osteochondral tissue comprises a vertebra.

5. The method of claim 1, wherein said composition is administered by injection.

6. The method of claim 1, wherein said composition is formulated as a biologic glue or cement.

* * * * *

UNITED STATES PATENT AND TRADEMARK OFFICE
CERTIFICATE OF CORRECTION

| | | |
|---|---|---|
| PATENT NO. | : 10,130,687 B2 | Page 1 of 1 |
| APPLICATION NO. | : 13/976617 | |
| DATED | : November 20, 2018 | |
| INVENTOR(S) | : Qian Chen et al. | |

It is certified that error appears in the above-identified patent and that said Letters Patent is hereby corrected as shown below:

In the Specification

At Column 1, Line numbers 14-21, at the ACKNOWLEDGEMENT OF GOVERNMENT SUPPORT section: Please replace the entire paragraph with the following:
ACKNOWLEDGEMENT OF GOVERNMENT SUPPORT
This invention was made with government support under AG014399 awarded by National Institutes of Health. The government has certain rights in the invention.

Signed and Sealed this
Eighteenth Day of August, 2020

Andrei Iancu
*Director of the United States Patent and Trademark Office*